(12) United States Patent
Liu et al.

(10) Patent No.: US 11,479,790 B2
(45) Date of Patent: Oct. 25, 2022

(54) INSECT-RESISTANT HERBICIDE-TOLERANT CORN TRANSFORMATION EVENT

(71) Applicant: CHINA NATIONAL SEED GROUP CORPORATION, LTD., Beijing (CN)

(72) Inventors: Bolin Liu, Beijing (CN); Qiuming She, Beijing (CN); Chao Tan, Beijing (CN); Jieting Xu, Beijing (CN); Xuxia Wang, Beijing (CN); Peixiuzi Tian, Beijing (CN); Dongming Nie, Beijing (CN); Yu Han, Beijing (CN); Chonglie Ma, Beijing (CN); Wanggen Zhang, Beijing (CN)

(73) Assignee: CHINA NATIONAL SEED GROUP CORPORATION, LTD., Beijing (CN)

( * ) Notice: Subject to any disclaimer, the term of this patent is extended or adjusted under 35 U.S.C. 154(b) by 160 days.

(21) Appl. No.: 16/968,067

(22) PCT Filed: Feb. 2, 2019

(86) PCT No.: PCT/CN2019/074611
§ 371 (c)(1),
(2) Date: Aug. 6, 2020

(87) PCT Pub. No.: WO2019/154373
PCT Pub. Date: Aug. 15, 2019

(65) Prior Publication Data
US 2021/0054402 A1 Feb. 25, 2021

(30) Foreign Application Priority Data
Feb. 11, 2018 (CN) .......................... 201810140851.4

(51) Int. Cl.
*C12N 15/82* (2006.01)
*C12Q 1/6895* (2018.01)

(52) U.S. Cl.
CPC ..... *C12N 15/8286* (2013.01); *C12N 15/8274* (2013.01); *C12N 15/8275* (2013.01); *C12Q 1/6895* (2013.01); *C12Q 2600/13* (2013.01)

(58) Field of Classification Search
CPC .. C12N 15/8286; C07K 14/325; C07K 14/32; C07K 2319/00
See application file for complete search history.

(56) References Cited

U.S. PATENT DOCUMENTS 8,735,560 B1 * 5/2014 English ............... C12N 15/8286
 435/468
2013/0031679 A1 1/2013 Beazley et al.
2015/0361446 A1 * 12/2015 Beatty ................. C07K 14/325
 435/6.12
2016/0160202 A1 6/2016 Babe et al.
2016/0186203 A1 6/2016 Narva et al.

FOREIGN PATENT DOCUMENTS

| CN | 1933723 A | 3/2007 |
| CN | 105886521 A | 8/2016 |
| CN | 106167818 A | 11/2016 |
| CN | 106916844 A | 7/2017 |
| CN | 107090464 A | 8/2017 |
| CN | 107109409 A | 8/2017 |
| CN | 107129992 A | 9/2017 |
| WO | WO 2016188332 A1 | 12/2016 |
| WO | WO 2017146899 A1 | 8/2017 |

OTHER PUBLICATIONS

White, et al.; A cassette containing the bar gene of *Streptomyces hygroscopicus*: a selectable marker for plant transformation; Nucleic Acids Research; Dec. 1989; vol. 18, No. 4; 1 pg.
Liu, et al.; Genetic Stability Analysis of Insect-resistant and Herbicide-tolerance Transgenic Maize Hill-NGc-1; Current Biotechnology; Jun. 2016; DOI:10.3969/j.issn.2095-2341; 8 pgs.
Xie, et al.; Survival Competition Ability of Transgenic Maize SK12-5 with Insect and Herbicide Resistance; Journal of Maize Sciences; 2017; 25(5):40-44; DOI:10.13597/j.cnki.maize.science.20170506; 5 pgs.
China National Intellectual Property Administration; Official Action of CN201810140851.4; dated Dec. 17, 2021; 10 pgs.
ISA/CN; International Search Report of PCT/CN2019/074611; dated Apr. 28, 2019; 4 pgs.

* cited by examiner

*Primary Examiner* — Weihua Fan
(74) *Attorney, Agent, or Firm* — Kilpatrick Townsend & Stockton LLP

(57) ABSTRACT

An insect-resistant herbicide-tolerant corn transformation event, and a related creation method, a detection method, and application thereof are provided herein. Using the corn inbred line Xiang 249 as a receptor, by means of agrobacterium-mediated genetic transformation, obtaining a corn plant with an exogenous gene insert inserted at a specific genomic locus, the exogenous gene insert comprising the following three genes: an insect-resistant gene, a glufosinate resistant gene, and a glyphosate resistant gene. In the obtained transformation event, the inserted exogenous genes are positioned at a non-functional locus of the corn genome, and do not affect the expression of the other genes of the receptor plant, such that the transgenic corn plant maintains good agronomic traits whilst acquiring insect resistance and herbicide tolerance.

12 Claims, 4 Drawing Sheets
Specification includes a Sequence Listing.

SEQUENCE LISTING

```
<160> NUMBER OF SEQ ID NOS: 11

<210> SEQ ID NO 1
<211> LENGTH: 11374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tgatggttaa tgaggcaaga tatgtgaatg gcaccttgaa tggtccactg cccgtctatg      60
agccgcagcc cgttgctctc aaagcaacta gcagcaggga ggcgctacca agcaagttag     120
cacaagtgga ggctgccggg ctcaatgagg atgagatggc gcttatcatc aagcgcttca     180
agaccgcgct aaaaggacgc aaggagtacc ccaacaagaa caagtcaagg ggaaaacgct     240
cctgcttcaa atgcggtaag aatggtcatt ttatagctca atgcctcgat aacgaatgac     300
caggcacaag agaagcatgg gaaaagagag aagaagaaga actaccggaa ggccaagggc     360
gaggcacaca ttgggaagga atgggactcc aactgctcct cctccgactc tgaggatgaa     420
ggactagctg cctcagcctt caacaaatct tcactcttcc ccaacgaacg ccatacatgc     480
cttatggcta aggagaagaa ggtatgtatt cgagacactc ctaagtactc ttcttctagc     540
gatgaggaat cttccgatga tgaggtagat tacactgatt tgtttaagga attatataga     600
gctaaagtag acaaaattaa tgaattaatt gatgctcttg atgaaaaaga taaactacaa     660
gaaaagcaag aggatatttt atatttgtgg tgtaaacaaa ttgacgctta gacaacttaa     720
taacacattg cggacgtttt taatgtactg aattaacgcc gaattaattc gggggatctg     780
```

```
gattttagta ctggattttg gttttaggaa ttagaaattt tattgataga agtattttac    840
aaatacaaat acatactaag ggtttcttat atgctcaaca catgagcgaa accctatagg    900
aaccctaatt cccttatctg gaactactc acacattatt atggagaaac tcgagtcaaa     960
tctcggtgac gggcaggacc ggacggggcg gtaccggcag gctgaagtcc agctgccaga    1020
aacccacgtc atgccagttc ccgtgcttga agccggccgc ccgcagcatg ccgcgggggg    1080
catatccgag cgcctcgtgc atgcgcacgc tcgggtcgtt gggcagcccg atgacagcga    1140
ccacgctctt gaagccctgt gcctccaggg acttcagcag gtgggtgtag agcgtggagc    1200
ccagtcccgt ccgctggtgg cgggggggaga cgtacacggt cgactcggcc gtccagtcgt    1260
aggcgttgcg tgccttccag gggcccgcgt aggcgatgcc ggcgacctcg ccgtccacct    1320
cggcgacgag ccagggatag cgctcccgca gacggacgag gtcgtccgtc cactcctgcg    1380
gttcctgcgg ctcggtacgg aagttgaccg tgcttgtctc gatgtagtgg ttgacgatgg    1440
tgcagaccgc cggcatgtcc gcctcggtgg cacggcggat gtcggccggg cgtcgttctg    1500
ggctcatggt agactcgaga gagatagatt tgtagagaga gactggtgat ttcagcgtgt    1560
cctctccaaa tgaaatgaac ttccttatat agaggaaggg tcttgcgaag gatagtggga    1620
ttgtgcgtca tcccttacgt cagtggagat atcacatcaa tccacttgct ttgaagacgt    1680
ggttggaacg tcttcttttt ccacgatgct cctcgtgggt gggggtccat ctttgggacc    1740
actgtcggca gaggcatctt gaacgatagc cttttccttta tcgcaatgat ggcatttgta    1800
ggtgccacct tcctttttcta ctgtcctttt gatgaagtga cagatagctg ggcaatggaa    1860
tccgaggagg tttcccgata ttacccttttg ttgaaaagtc tcaatagccc tttggtcttc    1920
tgagactgta tctttgatat tcttggagta gacgagagtg tcgtgctcca ccatgttcac    1980
atcaatccac ttgctttgaa gacgtggttg gaacgtcttc ttttttccacg atgctcctcg    2040
tgggtggggg tccatctttg ggaccactgt cggcagaggc atcttgaacg atagcctttc    2100
ctttatcgca atgatggcat ttgtaggtgc caccttcctt ttctactgtc ttttgatga    2160
agtgacagat agctgggcaa tggaatccga ggaggtttcc cgatattacc ctttgttgaa    2220
aagtctcaat agccctttgg tcttctgaga ctgtatcttt gatattcttg gagtagacga    2280
gagtgtcgtg ctccaccatg ttggcaagct gctctagcca atacgcaaac cgcctctccc    2340
cgcgcgttgg ccgattcatt aatgcagctg cacgacagg tttcccgact ggaaagcggg     2400
cagtgagcgc aacgcaatta atgtgagtta gctcactcat taggcacccc aggctttaca    2460
ctttatgctt ccggctcgta tgttgtgtgg aattgtgagc ggataacaat ttcacacagg    2520
aaacagctat gacatgatta cgaattcgag ctcggtaccc ggggatcctc tagagtcgac    2580
ctgcaggcat gcaagcttat ccagcttgca tgcctgcagt gcagcgtgac ccggtcgtgc    2640
ccctctctag agataatgag cattgcatgt ctaagttata aaaaattacc acatattttt    2700
tttgtcacac ttgtttgaag tgcagtttat ctatctttat acatatattt aaactttact    2760
ctacgaataa tataatctat agtactacaa taatatcagt gttttagaga atcatataaa    2820
tgaacagtta gacatggtct aaaggacaat tgagtatttt gacaacagga ctctacagtt    2880
ttatcttttt agtgtgcatg tgttctcctt ttttttgca aatagcttca cctatataat    2940
acttcatcca ttttattagt acatccattt agggtttagg gttaatggtt tttatagact    3000
aattttttta gtacatctat tttattctat tttagcctct aaattaagaa aactaaaact    3060
ctattttagt ttttttattt aataatttag atataaaata gaataaaata aagtgactaa    3120
aaattaaaca aatacccttt aagaaattaa aaaaactaag gaaacatttt tcttgtttcg    3180
```

```
agtagataat gccagcctgt taaacgccgt cgacgagtct aacggacacc aaccagcgaa    3240
ccagcagcgt cgcgtcgggc caagcgaagc agacggcacg gcatctctgt cgctgcctct    3300
ggacccctct cgagagttcc gctccaccgt tggacttgct ccgctgtcgg catccagaaa    3360
ttgcgtggcg gagcggcaga cgtgagccgg cacggcaggc ggcctcctcc tcctctcacg    3420
gcaccggcag ctacggggga ttcctttccc accgctcctt cgctttccct tcctcgcccg    3480
ccgtaataaa tagacacccc ctccacaccc tctttcccca acctcgtgtt gttcggagcg    3540
cacacacaca caaccagatc tcccccaaat ccaccgtcg gcacctccgc ttcaaggtac    3600
gccgctcgtc ctcccccccc ccctctctac cttctctaga tcggcgttcc ggtccatggt    3660
tagggcccgg tagttctact tctgttcatg tttgtgttag atccgtgttt gtgttagatc    3720
cgtgctgcta gcgttcgtac acggatgcga cctgtacgtc agacacgttc tgattgctaa    3780
cttgccagtg tttctctttg gggaatcctg ggatggctct agccgttccg cagacgggat    3840
cgatttcatg atttttttg tttcgttgca tagggtttgg tttgcccttt tcctttattt    3900
caatatatgc cgtgcacttg tttgtcgggt catcttttca tgcttttttt tgtcttggtt    3960
gtgatgatgt ggtctggttg ggcggtcgtt ctagatcgga gtagaattct gtttcaaact    4020
acctggtgga tttattaatt ttggatctgt atgtgtgtgc catacatatt catagttacg    4080
aattgaagat gatggatgga aatatcgatc taggataggt atacatgttg atgcgggttt    4140
tactgatgca tatacagaga tgcttttttgt tcgcttggtt gtgatgatgt ggtgtggttg    4200
ggcggtcgtt cattcgttct agatcggagt agaatactgt ttcaaactac ctggtgtatt    4260
tattaatttt ggaactgtat gtgtgtgtca tacatcttca tagttacgag tttaagatgg    4320
atggaaatat cgatctagga taggtataca tgttgatgtg ggttttactg atgcatatac    4380
atgatggcat atgcagcatc tattcatatg ctctaacctt gagtacctat ctattataat    4440
aaacaagtat gttttataat tattttgatc ttgatatact tggatgatgg catatgcagc    4500
agctatatgt ggattttttt agccctgcct tcatacgcta tttatttgct tggtactgtt    4560
tcttttgtcg atgctcaccc tgttgtttgg tgttacttct gcaggtcgac tctagaggat    4620
cgtattttta caacaattac caacaacaac aaacaacaaa caacattaca attactattt    4680
acaattacaa ccatggattg ccggccctac aactgcctgt cgaaccctga ggtggaggtc    4740
ctgggcggcg agcggattga gactggctac acaccgattg acatctcact ctccctgacc    4800
cagttcctcc tgtcggagtt cgtgccaggc gctgggttcg ttctcggcct ggtggatatc    4860
atttggggca tcttcgggcc aagccagtgg gacgctttcc tggtccagat cgagcagctc    4920
attaatcaga ggatcgagga gttcgcgcgg aaccaggcta ttagccgcct cgagggcctg    4980
tcgaacctct accagatcta cgccgagagc ttcaggagt gggaggctga tccgacgaac    5040
cccgccctga gggaggagat gcggattcag ttcaatgaca tgaactccgc tctgaccacg    5100
gctatcccac tcttcgcgt gcagaattac caggtcccac tcctgagcgt ctacgtgcag    5160
gctgcgaacc tccacctgtc tgtgctgcgc gatgtttcag tgttcggcca gacctggggg    5220
ttcgacgctg ctacgattaa ttccaggtac aacgatctga cacggctcat cggcaattac    5280
actgaccatg ccgttcggtg gtacaacacc ggcctcgaga gggtgtgggg gccagactcc    5340
agggattgga ttaggtacaa ccagttccgc agggagctca cactgactgt cctggacatc    5400
gtttccctct tcccaaacta cgatagccgg acctaccctta ttcgcacggt gtcccagctg    5460
acaagggaga tctacactaa tccagtcctc gagaacttcg acggctcttt ccgcgggtca    5520
```

```
gctcagggca ttgaggggtc catcaggagc cctcacctga tggatatcct caactcaatc    5580
accatctaca cggacgctca ccgcggcgag tactactggt ccgggcatca gatcatggct    5640
tccccagtcg gcttcagcgg gccagagttc accttccgac tgtacggcac gatggggaac    5700
gctgctccac agcagaggat cgttgctcag ctcggccagg gggtgtaccg cacactgtcc    5760
agcactctct accggcgccc gttcaacatc ggcattaaca atcagcagct gagcgtgctc    5820
gacggcacag agttcgccta cgggacttcg tctaacctgc cctcggcggt ctacaggaag    5880
tcgggcaccg ttgactctct cgatgagatc ccgccccaga acaataacgt cccacctcgc    5940
cagggcttct cgcacaggct gtcgcatgtt tctatgttcc ggtcaggctt ctccaactca    6000
tccgtctcca tcattagggc cccgatgttc tcatggatcc accggtccgc ggagttcaat    6060
aacatcattg ctagcgattc gatcacgcag attccagcgg tcaagggcaa tttcctcttc    6120
aacgggagcg ttatctcggg ccctgggttc acaggcgggg acctggtgag gctcaatagc    6180 tcggcaata acatccagaa caggcggtac attgaggtcc caatccactt cccttctacc    6240
tcaacgcgct acagggtccg ggttcgctac gcgtccgtga caccaattca tctgaatgtc    6300
aactggggca attcttcaat cttctcgaac actgtgcctg ccacagcgac ttctctggac    6360
aatctccagt ccagcgattt cggctacttc gagtctgcta acgccttcac ctcgtctctc    6420
ggcaatatcg tgggggtccg caacttcagc ggcacggctg gcgttattat tgataggttc    6480
gagttcatcc ctgttactgc taccctggag gctgagtaag taggtgagga attctttgag    6540
tattatggca ttggaaaagc cattgttctg cttgtaattt actgtgttct ttcagttttt    6600
gttttcggac atcaaaaaaa aaaaaaaaaa aaaaaaaaaa tttaacaaaa aaaaaaaaaa    6660
aaaaaaaaaa gtttaattcg attatcctcg agcgaatttc cccgatcgtt caaacatttg    6720
gcaataaagt ttcttaagat tgaatcctgt tgccggtctt gcgatgatta tcatataatt    6780
tctgttgaat tacgttaagc atgtaataat taacatgtaa tgcatgacgt tatttatgag    6840
atgggttttt atgattagag tcccgcaatt atacatttaa tacgcgatag aaaacaaaat    6900
atagcgcgca aactaggata aattatcgcg cgcggtgtca tctatgttac tagatcgggt    6960
ttagcttgaa ttcattatgt ggtctaggta ggtctatata taatgtcagt ctcagtgggg    7020
atttcatgtc cctgttacca atgcacccat attttggaaa caatgtaaaa agagttttat    7080
ccccataaaa ctctctctac tcccatgaaa ctttttatcat ctctctattc atcaatacgg    7140
tgtcacatca gcctatttaa tgcgtttaaa actctgatga aaccccactt agactggcct    7200
cagaaaactt gaaatgttct aaaaaaattc aagcccatgc atgattgaag caaacggtat    7260
agcaacggtg ttaacctggt ctagtgatct cttgtaatcc ttaacggcca cctaccgcag    7320
gtagcaaacg gcgtccccct cctcgatatc tccgcggcgg cctctggctt tttccgcgga    7380
attgcgcggt ggggacggat tccacgagac cgcgacgcaa ccgcctctcg ccgctgggcc    7440
ccacaccgct cggtgccgta gcctcacggg actctttctc cctcctcccc cgttataaat    7500
tggcttcatc ccctcccggc ctcatccatc caaatcccag tccccaatcc cagcccatcg    7560
tcggagaaat tcatcgaagc gaagcgaatc ctcgcgatcc tctcaaggta ctgcgagttt    7620
tcgatccccc tctcgacccc tcgtatgttt gtgttcgtcg tagcgtttga ttaggtatgc    7680
tttccctgtt tgtgttcgtc gtagcgtttg attaggtatg ctttccctgt tcgtgttcat    7740
cgtagtgttt gattaggtcg tgtgaggcga tggcctgcta gcgtccttcg atctgtagtc    7800
gatttgcggg tcgtggtgta gatctgcggg ccgtgatgaa gttatttggt gtgatcgtgc    7860
tcgcctgatt ctgcggggttg gctcgagtag atatgatggt tggaccggtt ggttcgttta    7920
```

-continued

```
ccgcgctagg gttgggctgg gatgatgttg catgcgccgt tgcgcgtgat cccgcggtag      7980
gacttgcgtt tgattgccag atctcgttac gattatgtga tttggtttgg acttttttaga    8040 tctgtagctt ctgcttatgt gccagatgcg cctactgctc atatgcctga tgataatcat    8100
aaatggctgt ggaactatgt atcagctaca ggtgtaggga cttgcgtcta attgtttggt    8160
cctgtactca tgttgcaatt atgcgattta gtttaggttg tttgttccac tcatctaggc    8220
tgtaaaaggg acactgctta gattgctgtt taatcttttt agtagattat attatattgg    8280
taacttatta cccttattac atgccatacg tgacttctgc tcatgcctga tgataatcat    8340
agatcactgt ggaattaatt agttgattgt tgaatcatgt ttcatgtaca taccatggca    8400
caattgctta gttccttaac aaatgcaaat tttactgatc catgtatgat ttgcgtggtt    8460
ctctaatgtg aaatactata gctacttgtt agtaagaatc aggttcgtat gcttaatgct    8520
gtatgtgcct tctgctcatg cctgatgata atcatatatc actggaatta attagttgat    8580
cgtttaatca tatatcaagt acataccatg gcacaatttt tagtcactta acccatgcag    8640
attgaactgg tccctgcatg ttttgctaaa ttgttctatt ctgattagac catatatcat    8700
gtattttttt tttggtaatg gttctcttat tttaaatgct atatagttct ggtacttgtt    8760
agaaagatct gcttcatagt ttagttgcct atccctcgaa ttaggatgct gagcagctga    8820
tcctatagct ttgtttcatg tatcaattct tttgtgttca acagtcagtt tttgttagat    8880
tcattgtaac ttatggtcgc ttactcttct ggtcctcaat gcttgcagct gcaggtcgac    8940
tctagaggat ccattttttac aacaattacc aacaacaaca aacaacaaac aacattacaa    9000
ttacatttac aattaccatg gctcagattc gcagcatggc tcagggcatt cagacactct    9060
cgctcaactc gtccaacctc agcaagactc agaaggggcc gctcgtgtcc aacagcctgt    9120
tcttcggctc gaagaagctc acgcagatca gcgcgaagtc gctgggcgtg ttcaagaagg    9180
acagcgtcct ccgcgtggtc aggaagtcca gcttccggat ctcggcttct gtggctaccg    9240
cggaggctca cggcgcctcg tctcgcccag ctaccgctag gaagtcatcc gggctgagcg    9300
gcacggtccg catccctggc gacaagtcaa tttcccatag gtcattcatg ttcggcgggc    9360
tcgcttccgg cgagacaagg atcactgggc tcctggaggg cgaggacgtg attaacacgg    9420
ggaaggctat gcaggcgatg ggcgctcgca tcaggaagga gggggacaca tggatcattg    9480
atggcgtcgg gaacggcggg ctcctggctc cagaggctcc tctggacttc gggaatgctg    9540
ctacaggctg ccgcctgact atggggctcg tcggcgtttta cgacttcgat tcgacattca    9600
tcggcgatgc ctctctcact aagaggccaa tgggccgggt gctgaaccct tcagggaga    9660 tgggcgtgca ggtcaagtcc gaggacgggg ataggctgcc agttaccctc aggggcccaa    9720
agacaccaac tccaatcacg taccgggtcc cgatggcttc cgctcaggtt aagagcgcgg    9780
tgctcctggc tgggctgaac accccgggca tcaccacggt catcgagccc attatgacac    9840
gcgaccacac tgagaagatg ctccaggggct tcggggcgaa tctcaccgtt gagacggacg    9900
ctgatggcgt gcggacaatc cgcctggagg gcaggggggaa gctcactggc caggtcatcg    9960
acgtcccagg cgaccctgtcc tccaccgctt tcccactggt ggctgctctc ctggtccctg    10020
gctccgacgt tactatcctg aacgtgctca tgaatccgac ccggacgggc ctcattctga    10080
ccctccagga gatgggcgcc gatatcgagg tcatcaaccc aaggctcgct ggcgggagg    10140 acgtcgccga tctgcgggtt cgctcttcaa ccctcaaggg cgttacggtg ccagaggaca    10200
gggctccttc catgatcgat gagtacccaa ttctggctgt cgcggctgcc ttcgctgagg    10260
```

```
gggccacggt catgaatggc ctggaggagc tgagggttaa ggagtctgac cggctctcag    10320
cggtggctaa cgggctgaag ctcaatggcg tggactgcga tgagggcgag acctctctgg    10380
ttgtgagggg gcggccggac ggcaaggggc tcggcaacgc tagcggcgcg gctgtggcta    10440
ctcacctcga tcataggatc gccatgagct tcctggtcat gggcctcgtt tcggagaatc    10500
cggtcacagt tgacgatgcc accatgattg cgacgtcctt ccccgagttc atggacctga    10560
tggctgggct gggggcgaag attgagctgt cggataccaa ggctgcgtga gagctcatcg    10620
aattccgaat tcccccgatc gttcaaacat ttggcaataa agtttcttaa gattgaatcc    10680
tgttgccggt cttgcgatga ttatcatata atttctgttg aattacgtta agcatgtaat    10740
aattaacatg taatgcatga cgttatttat gagatgggtt tttatgatta gagtcccgca    10800
attatacatt taatacgcga tagaaaacaa aatatagcgc gcaaactagg ataaattatc    10860
gcgcgcggtg tcatctatgt tactagatcg ggtttaaact atcagtgttt gacaagtttg    10920
ttagtgttca aaaatctctt gctttagaaa ttaagaaaaa tgaaatattg tcatctgagt    10980
tatcttcctg tcatgaatct attgctagct taaaggattt aaataatgat ttgaatacta    11040
agttagaaaa agcaaatgca actagttcat gtgtagaaca cgtagttatt tgcaatagat    11100
gtaaagatgt taattttgat gaacatgctg ctactattgc taagttaaat aatgatgttg    11160
caagtcttaa tgatcaattt aagacttgca aaaatgatta tgagaaatta aaatttgcta    11220
gggatgccta caccgttggt agacacccct caattaaaaa tgaacttggt tttcgaaagg    11280
aaaccaagaa cttaacaagc caaggacttc cgatctcaa ggggaaggg aaggctccta    11340 tggtcagtag ctcacgttcc tcacatgatc aaaa                                11374
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer CSP759

<400> SEQUENCE: 2
cacgcagatt ccagcggtca a                                                21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer CSP760

<400> SEQUENCE: 3
gacgaggtga aggcgttagc a                                                21

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      forward primer FW-Csp73

<400> SEQUENCE: 4
cagttcccgt gcttgaag                                                    18

<210> SEQ ID NO 5

```
<211> LENGTH: 19
<212> TYPE: DNA
<213> ORGANISM: Artificial Sequence
<220> FEATURE:
<223> OTHER INFORMATION: Description of Artificial Sequence: Synthetic
      reverse primer RV-Csp74

<400> SEQUENCE: 5
caccatcgtc aaccactac                                                    19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      forward primer FW-Csp1337

<400> SEQUENCE: 6
tctcgctcaa ctcgtccaac ct                                                22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      reverse primer RV-Csp1338

<400> SEQUENCE: 7
tctggcaccg taacgccctt ga                                                22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer FW-csp3758

<400> SEQUENCE: 8
tgatggttaa tgaggcaaga                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer RV-csp2344

<400> SEQUENCE: 9
tatagggttt cgctcatgtg                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer FW-csp3879

<400> SEQUENCE: 10
aagattgagc tgtcggatac                                                   20

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      reverse primer RV-csp3889

<400> SEQUENCE: 11
tttgatcatg tgaggaacgt                                                    20
```

INSECT-RESISTANT HERBICIDE-TOLERANT CORN TRANSFORMATION EVENT

CROSS-REFERENCE TO RELATED APPLICATIONS

The present application is a § 371 National Phase Application of PCT/CN2019/074611, filed Feb. 2, 2019, which application claims the priority under Article 8 of the PCT to Chinese Patent Application No. 201810140851.4, filed on Feb. 11, 2018, the entire contents of which are incorporated herein by reference in their entireties for all purposes herein.

SEQUENCE LISTING

The instant application contains a Sequence Listing which has been submitted electronically in ASCII format and is hereby incorporated by reference in its entirety. Said ASCII copy, created on Aug. 14, 2020, is named 093031-1203039-005000US_SL.txt and is 17,782 bytes in size.

TECHNICAL FIELD

The present application relates to the field of plant biotechnology, and more particularly, to a method for creating an insect-resistant herbicide-resistant maize transformation event, a detection method, and the application thereof.

BACKGROUND

Maize is an important feed and industrial raw material crop, which is the largest crop cultivated in China and is more than self-sufficient for a long time. However, the imports have been increasing year by year since 2010.

Corn borer, commonly known as maize worm, is one of the most important biological disasters causing the annual reduction of maize yields, which seriously affects the yields and quality of maize. The Corn borer includes the Asian corn borer (*Ostrinia furnacalis*) and the European corn borer (*Ostrinia nubilalis*). China is the prevalent and recurrent region of the Asian corn borer (*Ostrinia furnacalis*), which outbreaks on a large scale almost every two years. In a general year, maize yield is reduced by 10%-15% due to the damage caused by corn borer, and the yield can be reduced by more than 30% in a large-scale outbreak year, or even a total crop failure. Due to the damage caused by corn borer, 600-900 million tons of maize is lost each year. Corn borer not only directly causes loss of maize yield, but also induces and aggravates the occurrence of maize ear rot, causing the quality of maize to decrease. At present, the main control methods of corn borer are mainly pesticide control. The extensive use of pesticides not only increases planting costs but also destroys the ecological environment. Field weeds compete with crops for water, fertilizer, light energy, and growth space, and are also intermediate hosts of pathogens and pests that endanger crops, which are one of the key biological limiting factors for increase in the crop field. The area of crops seriously damaged by weeds in China is as high as 1.2 billion mu, of which maize accounts for 190 million mu. Currently, the widely used selective herbicides are applied in a large amount, and the residual period is long and the normal growth of the next crops is easily affected. Biocidal herbicides such as glufosinate have the characteristics of high efficiency, low toxicity, easy degradation, no residue, etc., but they have no selectivity for weeding and cannot be directly applied to the growth phase of crops. The plant transgenic breeding technology has the advantages of strong purpose, short cycle, high efficiency and the like, and can realize transfer of excellent genes among different species. Since the commercialization of the first transgenic crops in 1996, this technology has brought significant changes to the global agriculture.

In the case of transgenic maize, the main genes such as Cry1Ac and Cry1F control lepidopteran corn borer. In addition, a plurality of strains with coleopteran resistance, such as MON88017, are also introduced into commercial production, as well as strains resistant to maize rootworm, such as MON863, which are obtained by using Cry3-type genes.

More than 40 insect-resistant maize with transgenic Bt (such as MON810 and MON89034 of Monsanto, United States) have been approved by 26 countries for commercial production or feed processing in worldwide.

SUMMARY

In one aspect, the present application provides a nucleic acid molecule comprising: i) a sequence comprising the nucleotide positions 381-780 and/or 10815-11214 of SEQ ID NO: 1, or a fragment or a variant or a complement thereof; ii) a sequence comprising nucleotide positions 381-780 and 6239-6338 of SEQ ID NO: 1, or a fragment or a variant or a complement thereof; iii) a sequence comprising nucleotide positions 6239-6338 and 10815-11214 of SEQ ID NO: 1, or a fragment or a variant or a complement thereof, or iv) a sequence comprising the nucleotide positions 381-780, 6239-6338 and 10815-11214 of SEQ ID NO: 1, or a fragment or a variant or a complement thereof.

In one embodiment, a nucleic acid molecule provided herein comprises the sequence as set forth in SEQ ID NO: 1, or a fragment or a variant or a complement thereof.

In another embodiment, the present application provides a nucleic acid molecule comprising the following expression cassettes: a first expression cassette expressing a glufosinate-resistant gene, such as the sequence as set forth in nucleotide positions 748-2288 of SEQ ID NO: 1; a second expression cassette expressing an insect-resistant gene, such as the sequence as set forth in nucleotide positions 2620-6959 of SEQ ID NO: 1; and a third expression cassette expressing a glyphosate-resistant gene, such as the sequence as set forth in nucleotide positions 6968-10892 of SEQ ID NO: 1.

In another embodiment, a nucleic acid molecule provided herein is obtained by introducing into the genome of maize the following expression cassettes: a first expression cassette expressing a glufosinate-resistant gene, such as the sequence as set forth in nucleotide positions 748-2288 of SEQ ID NO: 1; a second expression cassette expressing an insect-resistant gene, such as the sequence as set forth in nucleotide positions 2620-6959 of SEQ ID NO: 1; and a third expression cassette expressing a glyphosate-resistant gene, such as the sequence as set forth in nucleotide positions 6968-10892 of SEQ ID NO: 1.

The nucleic acid molecules provided herein are present in maize plants, seeds, plant cells, progeny plants or plant parts.

In another aspect, the present application provides a probe for detecting a maize transformation event comprising the sequence as set forth in nucleotide positions 381-780 or 10815-11214 of SEQ ID NO: 1, or a fragment or a variant or a complement thereof.

The present application also provides a primer pair for detecting a maize transformation event that is capable of specifically amplifying the sequence as set forth in nucleotide positions 381-780 or 10815-11214 of SEQ ID NO: 1, or a fragment or a variant or a complement thereof.

In one embodiment, the primer pair is: i) a primer pair that specifically recognizes a sequence comprising nucleotide positions 381-780 of SEQ ID NO: 1; ii) a primer pair that specifically recognizes a sequence comprising nucleotide positions 10815-11214 of SEQ ID NO: 1; iii) a forward primer that specifically recognizes a sequence comprising nucleotide positions 381-780 of SEQ ID NO: 1, and a reverse primer that specifically recognizes a sequence comprising nucleotide positions 681-10915 of SEQ ID NO: 1; iv) a forward primer that specifically recognizes a sequence comprising nucleotide positions 681-10915 of SEQ ID NO: 1, and a reverse primer that specifically recognizes a sequence comprising nucleotide positions 10815-11214 of SEQ ID NO: 1.

In one embodiment, the primer pair provided herein is a nucleotide sequence as set forth in SEQ ID No:8 and SEQ ID No:9 or a complement thereof; or a nucleotide sequence as set forth in SEQ ID No:10 and SEQ ID No:11 or a complement thereof.

In addition, the present application also provides a kit or microarray for detecting a maize transformation event comprising the probes and/or the primer pairs as described above.

In yet another aspect, the present application provides a method of detecting a maize transformation event, comprising detecting the presence of the transformation event in a sample to be detected using the probes as described above; the primer pairs as described above; the probes and primer pairs as described above; or the kits or a microarrays as described above.

The present application also provides a method of breeding maize comprising the steps of: 1) obtaining maize comprising the nucleic acid molecule as described above; 2) obtaining maize plants, seeds, plant cells, progeny plants or plant parts from the maize obtained in step 1) by pollen culture, unfertilized embryo culture, doubling culture, cell culture, tissue culture, self-crossing or hybridization or a combination thereof; and, optionally, 3) identifying the resistance against the herbicides glufosinate and glyphosate as well as borer and/or armyworm of the progeny plants obtained in step 2), and detecting the presence or absence of the transformation event therein using the method as described above.

Further, the present application also provides a maize plant, a seed, a plant cell, a progeny plant or a plant part, and the like obtained by the above-mentioned method, and a product prepared from the maize plant, the seed, the plant cell, the progeny plant or the plant part, and the like, including a food, a feed or an industrial raw material, and the like.

Furthermore, the present application provides a method of controlling a population of lepidopteran pests comprising contacting the population of lepidopteran pests with a maize plant, seed, plant cell, progeny plant or plant part obtained by the above-mentioned method.

The application also provides a method of killing lepidopteran pests comprising contacting the lepidopteran pests with an insecticidally effective amount of a maize plant, seed, plant cell, progeny plant or plant part obtained by the above-mentioned method.

The present application also provides a method of reducing damage of lepidopteran pests to maize, comprising introducing into the genome of maize the following expression cassettes: a first expression cassette expressing a glufosinate-resistant gene, such as the sequence as set forth in nucleotide positions 748-2288 of SEQ ID NO: 1; a second expression cassette expressing an insect-resistant gene, such as the sequence as set forth in nucleotide positions 2620-6959 of SEQ ID NO: 1; and a third expression cassette expressing a glyphosate-resistant gene, such as the sequence as set forth in nucleotide positions 6968-10892 of SEQ ID NO: 1.

In a specific embodiment, the lepidopteran pests described in the above method are selected from the group consisting of *Ostrinia furnacalis, Ostrinia nubilalis* or *Mythimna separate* (Walker).

BRIEF DESCRIPTION OF THE DRAWINGS

FIG. 1 is a schematic structural diagram of the vector pZHZH35006, in which:

| | |
|---|---|
| Ubiquitin promoter | Ubiquitin gene promoter from maize |
| Ω sequence | Expression enhancer derived from tobacco mosaic virus gene |
| Kozak sequence | Present in eukaryotic mRNA for translation initiation |
| Cry1Ab/cry1AcZM | Optimized Bt gene sequence |
| polyA | Polyadenylation sequence |
| nos terminator | Agrobacterium nopaline synthase gene terminator |
| T-Border (right) | T-DNA right boundary sequence |
| CaMV 35S promoter | Cauliflower mosaic virus 35S promoter |
| bar | Glufosinate-resistant gene sequence |
| CaMV 35S terminator | Cauliflower mosaic virus 35S terminator |
| T-Border (left) | T-DNA left boundary sequence |
| Kanamycin (R) | Kanamycin resistance sequence |
| PBR322 ori | PBR322 start region sequence |
| PBR322 bom | PBR322 framework region sequence |
| PVS1 rep | PVS1 replicon |
| PVS1 sta | PVS1 Transcription Initiation Region |
| Cp4 epspsZM | Glufosinate-resistant gene sequence encoding EPSPS protein |
| Ω sequence 1 | Expression enhancer derived from tobacco etching virus gene |
| Ubiquitin4 promoter | Ubiquitin gene promoter from sugarcane |
| Bp | Base pair |

Figure 2:
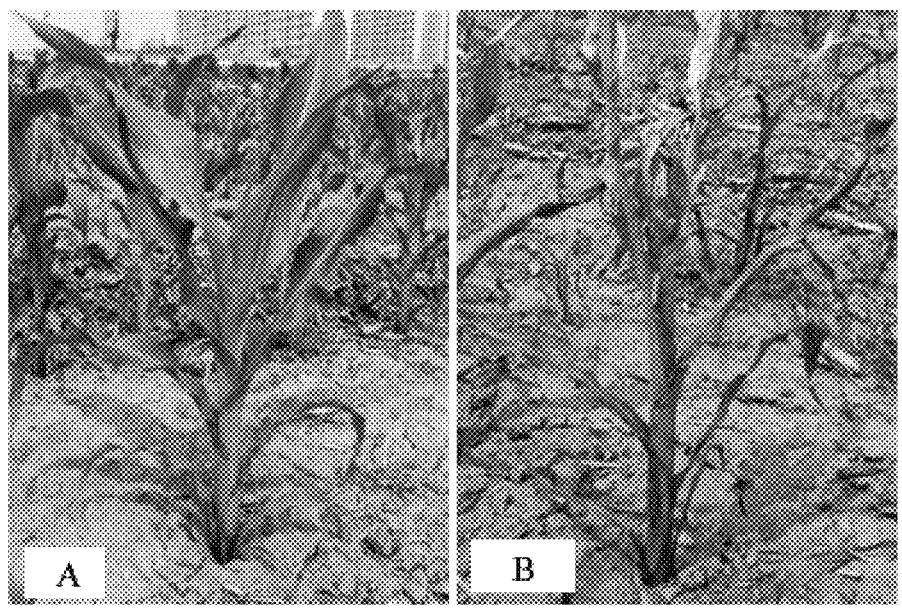

FIG. 2 is a photograph of plants at 4-5 days after spraying the glufosinate herbicide "Basta" in an amount of 250 ml/mu, in which:

A is ZZM030 which grew normally without any injured symptoms;

B is a non-transgenic negative control, wild-type Xiang 249, the leaves of which are dry, chlorotic and stagnant, showing significantly injured symptoms.

Figure 3:
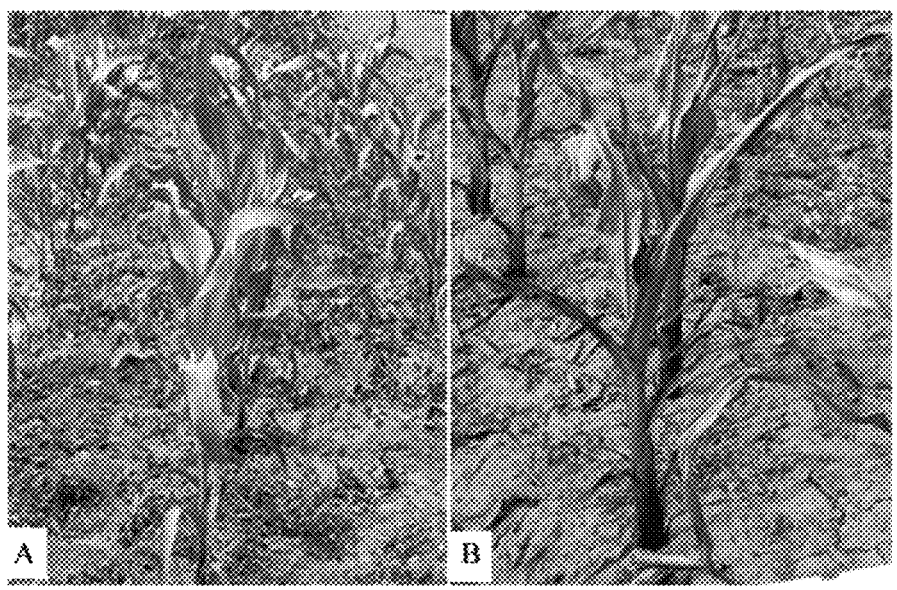

FIG. 3 is a photograph of plants at one week after spraying the glyphosate herbicide "Nongda" in an amount of 200 ml/mu, in which:

A is ZZM030 which grew normally without any injured symptoms;

B is a non-transgenic negative control, wild-type Xiang 249, the leaves of which are dry, chlorotic and stagnant, showing significant injured symptoms.

Figure 4:
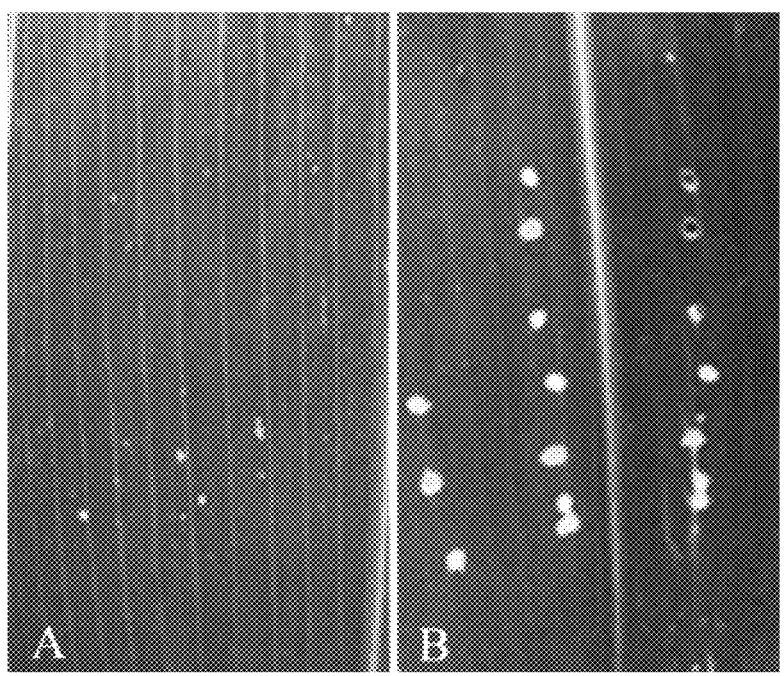

FIG. 4 is a photograph of a field experiment for the identification of corn borer resistance, with white spots as wormholes, in which:

A is the ZZM030 leaf with sparse and dispersed pinhole-sized wormholes;

B is a non-transgenic negative control, Xiang 249 leaf with mung bean-sized wormhole, with some leaves exhibiting short striped-holes.

Figure 5:
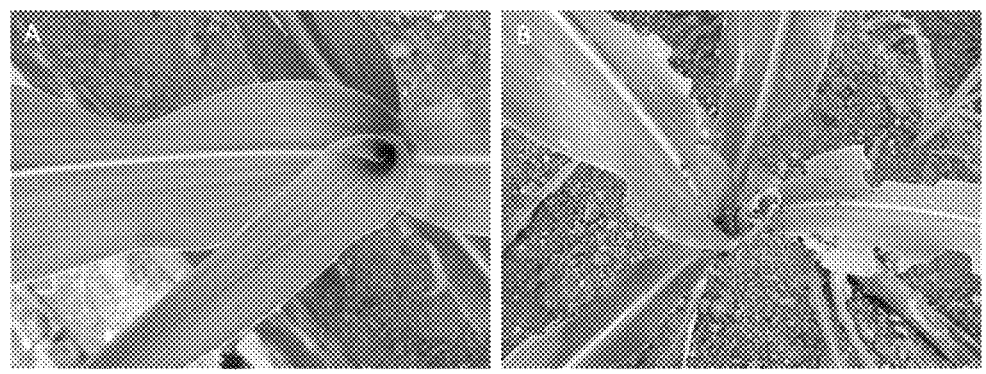

FIG. 5 is a photograph of a field experiment for identification of armyworm resistance. The edge of the leaf and the missing part of the leaf are the wormholes after being eaten by the armyworms, in which:

A is a ZZM030 leaf;

B is a non-transgenic negative control, wild-type Xiang 249 leaf.

Figure 6A:
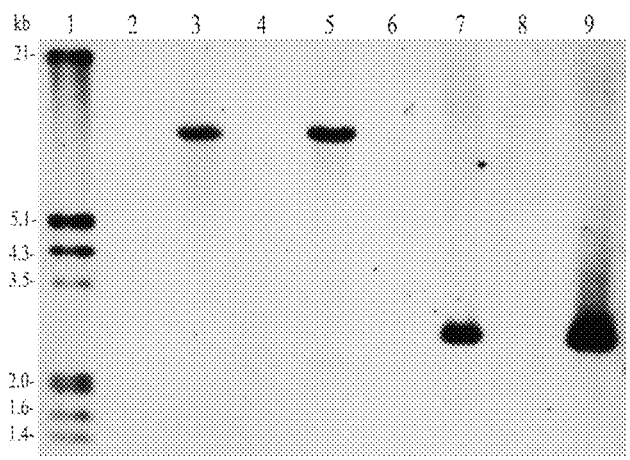
Figure 6B:
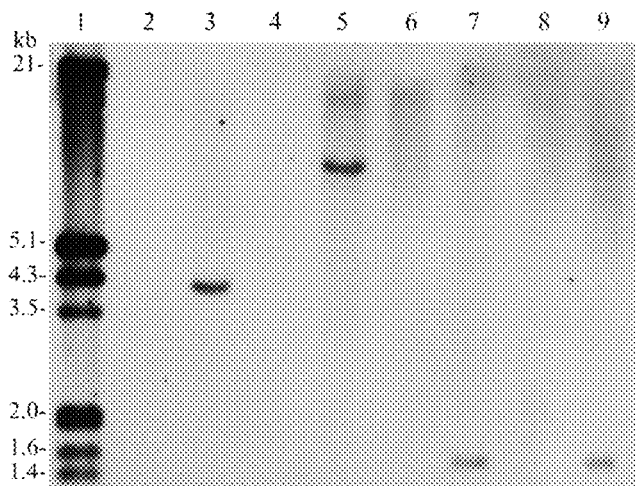
Figure 6C:
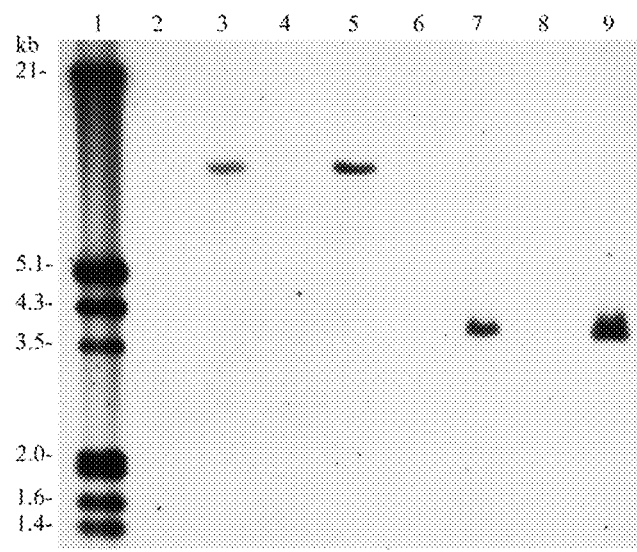

FIGS. 6A-6C are the copy number detection results of ZZM030 Southern blotting, in which:

FIG. 6A is the copy number detection result of cry1Ab/cry1AcZM gene insertion, in which: Lane 1, DNA molecular marker; Lane 2, blank; Lane 3, hybridization of HindIII-digested ZZM030 genomic DNA to cry1Ab/cry1AcZM-specific probe; Lane 4, hybridization of HindIII-digested wild-type Xiang 249 genomic DNA to cry1Ab/cry1AcZM-specific probe as a negative control; Lane 5, hybridization of KpnI-digested ZZM030 genomic DNA to cry1Ab/cry1AcZM-specific probe; Lane 6, hybridization of KpnI-digested wild-type Xiang 249 genomic DNA to cry1Ab/cry1AcZM-specific probe as a negative control; Lane 7, hybridization of EcoRI-digested ZZM030 genomic DNA to cry1Ab/cry1AcZM-specific probe as a positive control; Lane 8, hybridization of EcoRI-digested wild-type Xiang 249 genomic DNA to cry1Ab/cry1AcZM-specific probe as a negative control; Lane 9, hybridization of EcoRI-digested plasmid and wild-type Xiang 249 genomic DNA to cry1Ab/cry1AcZM-specific probe as a positive control;

FIG. 6B is the copy number detection result of bar gene insertion, in which: Lane 1, DNA molecular marker; Lane 2, blank; Lane 3, hybridization of HindIII-digested ZZM030 genomic DNA to bar-specific probe; Lane 4, hybridization of HindIII-digested wild-type Xiang 249 genomic DNA to bar-specific probe as a negative control; Lane 5, hybridization of EcoRI-digested ZZM030 genomic DNA to bar-specific probe; Lane 6, hybridization of EcoRI-digested wild-type Xiang 249 genomic DNA to bar-specific probe as a negative control; Lane 7, hybridization of KpnI-digested ZZM030 genomic DNA to bar-specific probe as a positive control; Lane 8, hybridization of KpnI-digested wild-type Xiang 249 genomic DNA to bar-specific probe as a negative control; Lane 9, hybridization of KpnI-digested plasmid and wild-type Xiang 249 genomic DNA to bar-specific probe as a positive control;

FIG. 6C is the copy number detection result of cp4 epspsZM gene insertion, in which: Lane 1, DNA molecular marker; Lane 2, blank; Lane 3, hybridization of HindIII-digested ZZM030 genomic DNA to cp4 epspsZM-specific probe; Lane 4, hybridization of HindIII-digested wild-type Xiang 249 genomic DNA to cp4 epspsZM-specific probe as a negative control; Lane 5, hybridization of KpnI-digested ZZM030 genomic DNA to cp4 epspsZM-specific probe; Lane 6, hybridization of KpnI-digested wild-type Xiang 249 genomic DNA to cp4 epspsZM-specific probe as a negative control; Lane 7, hybridization of EcoRI-digested ZZM030 genomic DNA to cp4 epspsZM-specific probe as a positive control; Lane 8, hybridization of EcoRI-digested wild-type Xiang 249 genomic DNA to cp4 epspsZM-specific probe as a negative control; Lane 9, hybridization of EcoRI-digested plasmid and wild-type Xiang 249 genomic DNA to cp4 epspsZM-specific probe as a positive control.

Figure 7A:
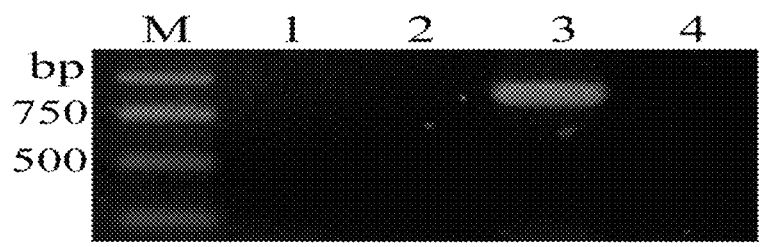
Figure 7B:
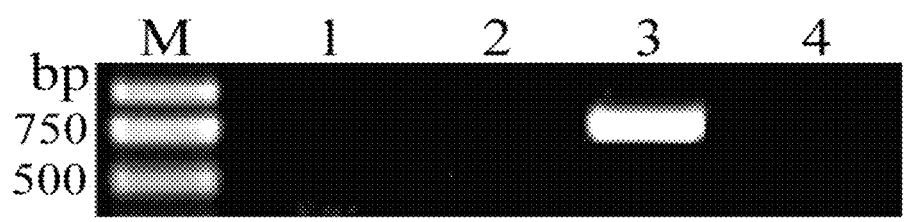

FIGS. 7A-7B are the specific PCR assay results of the ZZM030 event, in which:

FIG. 7A is the detection result of the left boundary;

FIG. 7B is the detection result of the right boundary;

wherein Lanes 1 to 4 are sterile water, Xiang 249 genomic DNA, ZZM030 genomic DNA, non-ZZM030 event genomic DNA obtained by transformation of the same vector, respectively.

DETAILED DESCRIPTION

The following definitions and methods are provided to better define the application and to guide those of ordinary skill in the art in the practice of the application. Unless otherwise indicated, the terms are to be understood in accordance with conventional usage by one of ordinary skill in the relevant art. All patent documents, academic papers, industry standards, and other publications cited herein are incorporated by reference in their entirety.

As used herein, "maize" is any maize plant and includes all plant varieties relating to maize breeding, including whole plants, plant cells, plant organs, plant protoplasts, plant cell tissue cultures from which plants can regenerate, plant calli, and intact plant cells in plants or plant parts such as embryos, pollens, ovules, seeds, leaves, flowers, branches, fruits, stems, roots, root tips, anthers, and the like.

It is well known to those skilled in the art that the expression of foreign genes in plants has a positional effect, i.e. is affected by the insertion of chromosomal positions, which may be due to chromosomal structures or transcriptional regulatory elements in the vicinity of integration sites. Thus, it is often desirable to produce hundreds of different transformation events and to screen out from these events excellent transformation events where the expression levels and patterns of foreign genes meet the expected requirements for commercial production applications.

Excellent transformation events can promote the transformation of foreign genes into germplasms having other genetic backgrounds by means of conventional breeding methods, i.e., sexual hybridization, and the progeny retain the transgenic expression characteristics of the original transformants. The present application relates to an excellent transformation event ZZM030 screened from a number of transformation events.

In the present application, "transformation event ZZM030" refers to a maize plant with an exogenous gene insert (T-DNA insert) inserted at a specific genomic site, which is obtained by Agrobacterium-mediated genetic transformation with the maize inbred line Xiang 249 as a recipient, where the exogenous gene insert comprises three genes: an insect-resistant gene, an glufosinate-resistant gene, and a glyphosate-resistant gene. The transformation event ZZM030 is obtained in the present application, in which the inserted foreign gene is located at the non-functional site of the maize genome, and does not affect the expression of other genes in the recipient plant itself, such that the transgenic maize plant maintains good agronomic traits while acquiring insect-resistant and herbicide-resistant properties.

In a specific example, the T-DNA insert obtained after the transgene has the sequence as set forth in nucleotide positions 681-10915 of SEQ ID NO: 1. The transformation event ZZM030 may refer to such a transgenic process, or may refer to a T-DNA insert within the genome resulting from this process, or a combination of a T-DNA insert and flanking sequences, or may refer to a maize plant resulting from this transgenic process. The transformation event ZZM030 may also refer to a progeny plant obtained by asexual reproduction, sexual reproduction, aneuploidy reproduction or doubling reproduction or a combination thereof.

In other embodiments, this event is also applicable to plants obtained by transforming other plant recipient species with the same foreign gene (the sequence as set forth in nucleotide positions 681-10915 of SEQ ID NO: 1), thereby inserting the T-DNA insert into the same genomic location.

Suitable plants include monocotyledonous plants such as rice, wheat, oats, barley, highland barley, millet, sorghum and sugarcane, and the like.

In the present application, a T-DNA insert (nucleotide positions 681-10915) was obtained with the nucleotide positions 1-680 of SEQ ID NO: 1 as the left flanking sequence and the nucleotide positions 10916-11375 of SEQ ID NO: 1 as the right flanking sequence. The flanking sequences are not limited to nucleotide positions 1-680 and 10916-11375 of SEQ ID NO: 1, as the flanking sequences are listed only to indicate the position of the T-DNA insert in the genome, i.e., the left insertion point of the T-DNA insert is located on chromosome 4 40636901 bp; and the right insertion point of the T-DNA insert is located on chromosome 4 40636883 bp. Thus, the flanking sequences of the present application may extend to both ends according to the genomic sequence, i.e., the left flanking sequence may extend to downstream of chromosome 4 40636901 bp and the right flanking sequence may extend to upstream of chromosome 4 40636883 bp.

Since the transformation event ZZM030 produces a T-DNA insert inserted at a specific site in the genome, its insertion site is specific and can be used to detect whether the transformation event ZZM030 is contained in a biological sample. In particular embodiments, any sequences comprising the junction site of the T-DNA insert with the flanking sequences of the transformation event ZZM030 can be used to detect the transformation event ZZM030 of the present application, including, but not limited to, one or more of the following sequences comprising the upstream insertion site (the junction site of the left flanking sequence with the T-DNA insert) or the downstream insertion site (the junction site of the right flanking sequence with the T-DNA insert), or a fragment or a variant or a complement thereof: i) a sequence comprising nucleotide positions 381-780 of SEQ ID NO: 1; ii) a sequence comprising nucleotide positions 1-898 of SEQ ID NO: 1; iii) a sequence comprising nucleotide positions 6239-6338 of SEQ ID NO: 1; iv) a sequence comprising nucleotide positions 10815-11214 of SEQ ID NO: 1; v) a sequence comprising nucleotide positions 10578-11373 of SEQ ID NO: 1; vi) a sequence comprising nucleotide positions 381-11241 of SEQ ID NO: 1; vii) a sequence comprising SEQ ID NO: 1.

In a specific example, a sequence that can be used to detect a transformation event ZZM030 of the present application is a sequence comprising an upstream insertion site or a fragment or a variant or a complement thereof, such as a sequence comprising nucleotide positions 381-780 of SEQ ID NO: 1 or a sequence comprising nucleotide positions 1-898 of SEQ ID NO: 1; or a sequence comprising a downstream insertion site, such as a sequence comprising nucleotide positions 10815-11214 of SEQ ID NO: 1 or a sequence comprising nucleotide positions 10578-11373 of SEQ ID NO: 1; or a sequence comprising the combination of an upstream insertion site and a downstream insertion site.

In another example, a sequence that can be used to detect the transformation event ZZM030 of the present application is a combination of a sequence comprising an upstream insertion site or a fragment or a variant or a complement thereof and a sequence comprising a T-DNA insert or a fragment or a variant or a complement thereof, for example, the combination of a sequence comprising nucleotide positions 381-780 of SEQ ID NO: 1 or a sequence comprising nucleotide positions 1-898 of SEQ ID NO: 1, and a sequence comprising nucleotide positions 6239-6338 of SEQ ID NO: 1 or a sequence comprising nucleotide positions 681-10915 of SEQ ID NO: 1.

In another example, a sequence that can be used to detect the transformation event ZZM030 of the present application is a combination of a sequence comprising a downstream insertion site or a fragment or a variant or a complement thereof and a sequence comprising a T-DNA insert or a fragment or a variant or a complement thereof, for example, the combination of a sequence comprising nucleotide positions 10815-11214 of SEQ ID NO: 1 or a sequence comprising nucleotide positions 10578-11373 of SEQ ID NO: 1, and a sequence comprising nucleotide positions 6239-6338 of SEQ ID NO: 1 or a sequence comprising nucleotide positions 681-10915 of SEQ ID NO: 1.

In another example, a sequence that can be used to detect the transformation event ZZM030 of the present application is a sequence comprising nucleotide positions 381-11241 of SEQ ID NO: 1 or a fragment or a variant or a complement thereof or a sequence comprising SEQ ID NO: 1 or a fragment or a variant or a complement thereof.

Thus, primer pairs, probes, and combinations of primer pairs and probes capable of specifically detecting the junction site of the T-DNA insert with the flanking sequences of the transformation event ZZM030 can be used to detect the transformation event ZZM030 of the present application.

As used herein, "nucleotide sequence" includes deoxyribonucleotide or ribonucleotide polymers in single- or double-stranded forms, and unless otherwise limited, nucleotide sequences are written from left to right in the 5' to 3' direction.

In some embodiments, the present application also relates to a fragment of a nucleic acid sequence that refers to a portion of an incomplete smaller fragment in an intact portion. For example, a fragment of SEQ ID NO: 1 includes a sequence of at least about 10 nucleotides, at least about 20 nucleotides, at least about 30 nucleotides, at least about 40 nucleotides, or at least about 50 nucleotides or more of the entire sequence of SEQ ID NO: 1.

In some embodiments, the nucleic acid sequences of the present application may be altered to produce conservative amino acid substitutions. In certain embodiments, nucleotide sequences of the present application may be replaced according to monocotyledonous codon preference without altering the amino acid sequence, e.g., a codon encoding the same amino acid sequence may be substituted with a codon preferred by a monocotyledonous plant without altering the amino acid sequence encoded by the nucleotide sequence. In some embodiments, the present application also relates to variants of nucleic acid sequences. In general, a variant of a particular nucleic acid fragment will have at least about 70%, 75%, 80%, 85%, 86%, 87%, 88%, 89%, 90%, 91%, 92%, 93%, 94%, 95%, 96%, 97%, 98%, 99%, 99.5%, or 99.9% or more sequence identity to the particular nucleic acid sequence, or a complement thereof. Such variant sequences include additions, deletions or substitutions of one or more nucleotides, thereby resulting in the additions, deletions or substitutions of the corresponding amino acid residues. Sequence identity can be determined by sequence alignment procedures known in the art, including hybridization techniques. The nucleotide sequence variants in some embodiments may differ from the sequences of the present application by as little as 1 to 15 nucleotides, as little as 1 to 10 (e.g., 6 to 10), as little as 5, as little as 4, 3, 2, or even 1 nucleotides.

As used herein, a "probe" is an isolated polynucleotide that is complementary to the strand of the target polynucleotide attached to a conventionally detectable label or reporter such as a radioisotope, a ligand, a chemiluminescent agent, or an enzyme.

In particular embodiments, a DNA probe for detecting the transformation event ZZM030 provided herein comprises a sequence comprising sufficient length of contiguous nucleotides of SEQ ID NO: 1 or a fully complementary sequence thereof. The DNA probe hybridizes under stringent hybridization conditions to a nucleotide sequence comprising an upstream insertion site or a downstream insertion site, and does not hybridize under stringent hybridization conditions to a nucleotide sequence not comprising an upstream insertion site or a downstream insertion site.

In a specific example, a probe provided herein comprises the sequence as set forth in nucleotide positions 381-780 or 10815-11214 of SEQ ID NO: 1, or a fragment or a variant or a complement thereof. As used herein, a "primer" is an isolated polynucleotide that anneals to a complementary target DNA strand to form a hybrid between the primer and the target DNA strand by nucleic acid hybridization, and then extends along the target DNA strand by the aid of, for example, a DNA polymerase. Primer pairs relate to the use of their target polynucleotide amplification, for example by polymerase chain reaction (PCR) or other conventional nucleic acid amplification methods.

In particular embodiments, a primer pair for detecting the transformation event ZZM030 provided herein comprises a first DNA molecule and a second DNA molecule different from the first DNA molecule, wherein the first DNA molecule and the second DNA molecule each comprise a nucleotide sequence of sufficient length of contiguous nucleotides of SEQ ID NO: 1 or a complete complement thereof, and the first DNA molecule is present in the T-DNA insert of SEQ ID NO: 1 and the second DNA molecule is present in the flanking sequences of SEQ ID NO: 1. When used together with DNA from the transformation event ZZM030 in an amplification reaction, the DNA primer pair generates an amplicon for detecting the transformation event ZZM030 DNA in a sample. The amplicon comprises the sequence as set forth in the nucleotide positions 381-780 or 10815-11214 of SEQ ID NO: 1, or a fragment or variant or complement thereof.

In a specific embodiment, a primer pair provided herein is a primer pair that specifically recognizes a sequence comprising nucleotide positions 381-780 or 1-898 of SEQ ID NO: 1.

In a specific embodiment, a primer pair provided herein is a primer pair that specifically recognizes a sequence comprising nucleotide positions 10815-11214 or 10578-11373 of SEQ ID NO: 1.

In particular embodiments, the primer pairs provided herein are i) a primer pair that specifically recognizes a sequence comprising nucleotide positions 381-780 or 1-898 of SEQ ID NO: 1; and ii) a primer pair that specifically recognizes a sequence comprising nucleotide positions 10815-11214 or 10578-11373 of SEQ ID NO: 1; Alternatively, the primer pair comprises a forward primer that specifically recognizes a sequence comprising nucleotide positions 381-780 or 1-898 of SEQ ID NO: 1, and a reverse primer that specifically recognizes a sequence comprising nucleotide positions 10815-11214 or 10578-11373 of SEQ ID NO: 1.

In another specific embodiment, the primer pairs provided herein are i) a primer pair that specifically recognizes a sequence comprising nucleotide positions 381-780 or 1-898 of SEQ ID NO: 1; and ii) a primer pair that specifically recognizes a sequence comprising nucleotide positions 6239-6338 or 681-10915 of SEQ ID NO: 1; alternatively, the primer pair comprises a forward primer that specifically recognizes a sequence comprising nucleotide positions 381-780 or 1-898 of SEQ ID NO: 1, and a reverse primer that specifically recognizes a sequence comprising nucleotide positions 6239-6338 or 681-10915 of SEQ ID NO: 1.

In another specific embodiment, the primer pairs provided herein are i) a primer pair that specifically recognizes a sequence comprising nucleotide positions 6239-6338 or 681-10915 of SEQ ID NO: 1; and ii) a primer pair that specifically recognizes a sequence comprising nucleotide positions 10815-11214 or 10578-11373 of SEQ ID NO: 1; Alternatively, the primer pair comprises a forward primer that specifically recognizes a sequence comprising nucleotide positions 6239-6338 or 681-10915 of SEQ ID NO: 1, and a reverse primer that specifically recognizes a sequence comprising nucleotide positions 10815-11214 or 10578-11373 of SEQ ID NO: 1.

In another specific embodiment, the primer pairs provided herein are i) a primer pair that specifically recognizes a sequence comprising nucleotide positions 381-780 or 1-898 of SEQ ID NO: 1, ii) a primer pair that specifically recognizes a sequence comprising nucleotide positions 6239-6338 or 681-10915 of SEQ ID NO: 1, and iii) a primer pair that specifically recognizes a sequence comprising nucleotide positions 10815-11214 or 10578-11373 of SEQ ID NO: 1.

In another specific embodiment, a primer pair provided herein is a primer pair that specifically recognizes a sequence comprising SEQ ID NO: 1.

In a specific example, the primer pair is the nucleotide sequence as set forth in SEQ ID No:8 and SEQ ID No:9 or a complement thereof or the nucleotide sequence as set forth in SEQ ID No:10 and SEQ ID No:11 or a complement thereof.

Methods for designing and using primers and probes are well known in the art, such as those described in Sambrook et al., Molecular Cloning Laboratory Manual (Sambrook J & Russell D W, Molecular cloning: a laboratory manual, 2001) and in Wiley-Blackwell, Current Protocols in Molecular Biology.

As used herein, "kit" or "microarray" refers to a group of reagents or chip for identification and/or detection of maize transformation events ZZM030 in biological samples. For purposes of quality control (e.g., purity of seed batches), detection of the event ZZM030 in plant materials or materials comprising or derived from plant materials such as, but not limited to, food or feed products, kits or chips may be used, and the components therein may be specifically adjusted.

In particular embodiments, the kits or probes provided herein comprise any of the probes or any of the primer pairs provided herein. In another specific embodiment, the kits or probes provided herein comprise the combination of any of the probes of any of primer pairs provided herein.

In addition, the present application also provides transgenic maize plants, progeny, seeds, plant cells or plant parts and the products thereof, including but not limited to food, feed or industrial raw materials. These plants, progeny, seeds, plant cells, plant parts, and the products thereof all contain a detectable nucleic acid molecules of the junction sites of T-DNA insert with the flanking sequences provided herein.

Further, the present application also provides a method of breeding maize comprising the steps of: 1) obtaining maize comprising a nucleic acid molecules of the junction sites of T-DNA insert with the flanking sequences provided herein; 2) obtaining progeny plants, seeds, plant cells, progeny plants or plant parts from the maize obtained in step 1) by pollen culture, unfertilized embryo culture, doubling culture, cell culture, tissue culture, self-crossing or hybridization or a combination thereof; and, optionally, 3) identifying the resistance against the herbicides glufosinate and glyphosate as well as insects of the maize plants obtained in step 2), and detecting the presence or absence of the transformation event ZZM030 therein using the probes, primer pairs, kits or arrays provided herein.

In addition, the present application provides a method of controlling weeds in the field, and a method of controlling or killing lepidopteran pests.

In particular embodiments, the present application provides a method of controlling weeds in a field, comprising growing a maize plant comprising the transformation event ZZM030 in the field, and applying to the field an effective amount of herbicides glyphosate and glufosinate capable of controlling weeds without harming the transgenic maize plant comprising the event ZZM030.

In particular embodiments, the method of controlling or killing a lepidopteran pest provided herein comprises contacting the lepidopteran pest with an effective amount of a maize plant of transformation event ZZM030, or feeding the lepidopteran pest with an effective amount of a maize plant of transformation event ZZM030, or making the lepidopteran pest have an effective amount of a maize plant of transformation event ZZM030. The lepidopteran pests include, but are not limited to, Ostrinia furnacalis, Ostrinia nubilalis, Mythimna separate (Walker), and the like.

As used herein, an "effective amount" or "insecticidally effective amount" refers to the amount of an insecticidally active substance or organism in the environment of pests.

Examples

The following examples can illustrate the invention, but are not intended to limit the scope of the invention. Modifications or alternations to the methods, steps or conditions of the present invention are intended to fall within the scope of the present application without departing from the spirit and essence of the invention.

Unless otherwise specified, the examples were performed according to routine experimental conditions, such as the Molecular Cloning Experiment Manual by Sambrook et al. (Sambrook J & Russell D W, Molecular cloning: a laboratory manual, 2001), or as suggested in the manufacturer's specification.

Unless otherwise specified, the chemical reagents used in the examples are conventional commercially available reagents, and the technical means used in the examples are conventional means well known to those skilled in the art.

Materials of maize varieties related in the following examples are all provided by China National Seed Group Corporation, Ltd., in which the maize inbred line Xiang 249 is the female parent of the maize variety Changcheng 799. The Xiang 249 was selectively cultivated from the maize germplasm resources imported from abroad by pedigree self-cross separation and strict selection after 10 generations in 1996.

Example 1. Vector Construction

1. Synthesis of Insect-Resistant Gene

The insect-resistant gene cry1Ab/cry1AcZM disclosed by the applicant in PCT International Application No. WO2017012577A1, which was expressed in plants and produced an insect-resistant effect, was employed. The gene was genetically engineered from 608-amino acid sequence at the N-terminal end of a fused and engineered Cry1Ab and Cry1Ac, in which the coding sequence was replaced with plant-preferred codons, and AT-rich sequences in the DNA sequence that cause plant transcription instability and common restriction sites were corrected and eliminated by a method for replacing codons. Meanwhile, a 67-nucleotide Ω sequence and a 3-nucleotide (ACC) Kozak sequence were added to the 5' end of the gene to enhance the translation efficiency of eukaryotic genes. The 135 bp polyA sequence was added to the 3' end of the gene. The protein encoded by this gene contains three functional regions with the N-terminal two functional regions highly homologous to the corresponding portion of Cry1Ab and the C-terminal functional region highly homologous to Cry1Ac. The insect-resistant gene cry1Ab/cry1AcZM as set forth in nucleotide positions 4624 to 6670 of SEQ ID NO:1 was synthesized.

2. Synthesis of Exogenous Herbicide-Resistant Gene

The coding region sequence of the glyphosate-resistant gene cp4 epsps was optimized according to maize codon preference by using the Vector NTI software, and the expression enhancer Ω sequence1 was added at the 5' end. The modified DNA sequence was designated as cp4 epspsZM. The glyphosate-resistant gene as set forth in nucleotide positions 8954 to 10611 of SEQ ID NO: 1 was synthesized.

Bar gene sequence was shown in Gene bank accession number X17220.1. The glufosinate-resistant gene as set forth in nucleotide positions 957 to 1508 of SEQ ID NO: 1 was synthesized.

3. Vector Construction

HindIII and PstI restriction sites were added to the 5' end of the synthesized cry1Ab/cry1AcZM, and PmeI restriction site was added to the 3' end. The synthesized sequence was cloned into a Puc57 simple vector, which was designated as pZZ01194.

The intermediate vector pZZ00005 containing ubiquitin promoter (with HindIII restriction site at the 5' end and BamHI restriction site at the 3' end) was digested with restriction enzymes HindIII and BamHI, and the resulting sticky ends were blunted with T4 DNA polymerase to obtain an ubiquitin promoter fragment.

PZZ01194 was digested with restriction enzyme PstI, the resulting sticky ends were blunted with T4 DNA polymerase, and the ubiquitin promoter was ligated by blunt end ligation to obtain a vector containing an ubiquitin promoter—cry1Ab/cry1AcZM fragment, designated as pZZ01201.

The intermediate vector pZZ01188 containing nos terminator (with EcoRI restriction site at the 5' end and PmeI and EcoRI restriction sites at the 3' end) was digested with restriction enzyme EcoRI, and the resulting sticky ends were blunted with T4 DNA polymerase to obtain the nos terminator sequence.

pZZ01201 was digested with PmeI and the nos terminator was ligated by blunt end ligation to obtain a vector containing the ubiquitin promoter—cry 1Ab/cry 1AcZM—nos terminator fragment, designated as pZZ01205.

For the intermediate vector pZZ00015 (containing CaMV 35S promoter—bar—CaMV 35S terminator and ubiquitin promoter—egfp—nos terminator expression element), ubiquitin promoter-egfp-nos terminator was removed by restriction enzymes HindIII and PmeI. The pZZ01205 vector was digested with restriction enzymes HindIII and PmeI to obtain ubiquitin promoter—cry1Ab/cry1AcZM—nos terminator fragment. The two fragments were ligated to obtain an expression vector containing two expression cassettes, ubiquitin promoter—cry1Ab/cry1AcZM—nos terminator and CaMV 35S promoter—bar—CaMV 35S terminator, designated as pZHZH25017.

The intermediate vector pZZ01337 (CaMV 35S promoter—cp4 epspsZM—nos terminator) was digested using restriction enzymes HindIII and BamHI to remove CaMV 35S promoter. The intermediate vector pZZ00033 was digested using restriction enzymes HindIII and BamHI to obtain Ubiquitin4 promoter. The two fragments were ligated to obtain a vector containing the ubiquitin4 promoter—cp4 epspsZM—nos terminator fragment, designated as pZZ01383.

PZZ01383 was digested with restriction enzymes HindII and PmeI to obtain the ubiquitin4 promoter —cp4 epspsZM—nos terminator fragment, and the resulting sticky ends were blunted with T4 DNA polymerase.

Figure 1:
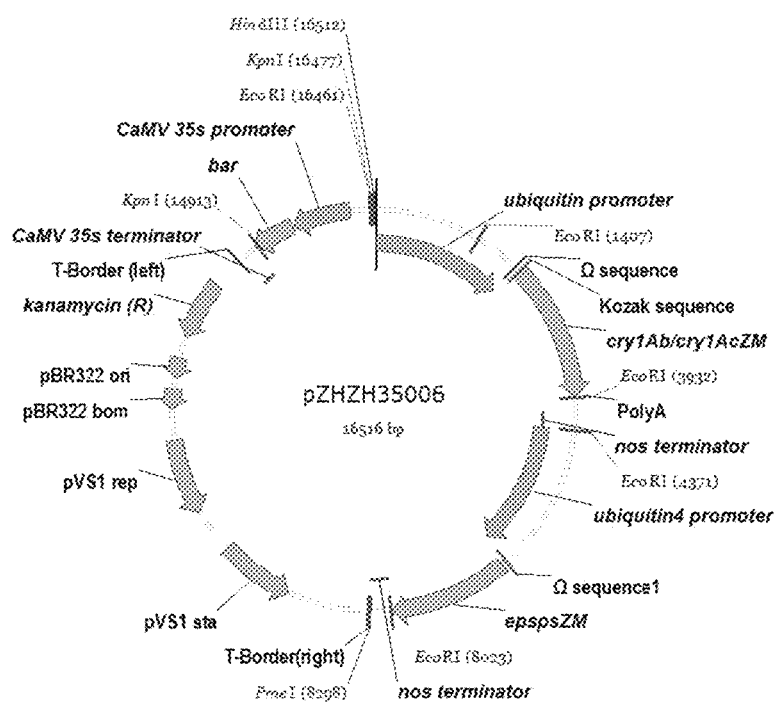

PZHZH25017 was digested with restriction enzyme PmeI and ubiquitin4 promoter-cp4 epspsZM—nos terminator was ligated by blunt end ligation to obtain a plant expression vector containing three expression cassettes, ubiquitin promoter—cry1Ab/cry1AcZM—nos terminator, CaMV 35S promoter bar—CaMV 35S terminator and ubiquitin4 promoter—cp4 epspsZM—nos terminator, designated as pZHZH35006, the physical map of which is shown in FIG. 1.

Example 2. Obtaining Transgenic Maize

Transgenic maize was obtained using Agrobacterium-mediated genetic transformation.

The plasmid DNA of the vector pZHZH35006 was transformed into Agrobacterium EHA105 by electroporation and identified for later use.

The transformation was carried out using the efficient transgenic method of the maize backbone inbred line disclosed by the applicant in the CN Patent Application CN104745622A.

Specifically, immature embryos about 1.5 mm in length of the maize inbred line Xiang 249 after self-crossing was used for transformation. Immature embryos of about 200 ears were collected in one batch, and placed in an EP tube following by removing of the suspension. Agrobacterium broth containing 200 µM acetosyringone was added, co-cultured for 5 min, and the immature embryos were then transferred onto the co-culture medium and cultured in the dark for 3 days. The immature embryos cultured in the dark were placed on a callus induction medium, and after callus growth, they were placed on a screening medium containing 5 mg/L Bialaphos to be screened and cultured, and passaged once every two weeks. When the resistant calli came out, the embryogenic calli in good condition were selected and transferred to the differentiation medium under the culture condition of 3000 Lux light intensity per day, 16 h light at 26° C., and regenerated plantlets appeared two weeks later. The regenerated plantlets were transferred to the rooting medium, and after secondary roots grew from the plantlets, they were transplanted into pots mixed with nutrient soil and vermiculite (1:3).

The obtained transformed plantlets were test according to the following procedure to screen out transgenic positive plants.

(1) DNA Extraction

Genomic DNA was extracted from maize using DNAsecure Plant Kit novel plant genomic DNA extraction kit (centrifugal column type) from Tiangen Biochemical Technology Inc.

(2) PCR

The following reagents at −20° C. were thawed: 10-fold PCR buffer (Takara), deoxynucleotide mixture (10 mM, Sigma), forward primer SEQ ID NO: 2 (CSP759): 5'-CACGCAGATTCCAGCGGTCAA-3', reverse primer SEQ ID NO: 3 (CSP760): 5'-GACGAGGTGAAGGCGT-TAGCA-3' and maize leaf DNA template. All the reagents were centrifuged for several seconds after thawing, and placed on ice for later use. A mixture of PCR reaction system was prepared, mixed and centrifuged for several seconds. PCR reaction system (20 µL): 2 µL 10-fold PCR buffer (Takara), 0.5 µLdeoxynucleotide mixture (10 mM, Sigma), 0.8 µL forward and reverse primer mixture (5 µM), 0.2 µL r-Taq (5U, Takara), the remaining dd H$_2$O. The mixture was placed into PCR tubes of 200 µL, and 1 µL maize leaf DNA template was added. Different samples were separately marked for differentiation. The PCR reaction tubes were placed in a ABI 9700-type PCR amplification apparatus, and a preset PCR amplification program was selected to start the reaction. The PCR reaction procedure was: pre-denaturation at 94° C. for 2 min; 30 cycles: denaturation at 94° C. for 30 sec, annealing at 58° C. for 30 sec, extension at 72° C. for 30 sec; and finally extension at 72° C. for 5 min.

(3) Agarose Gel Electrophoresis Detection

After completion of PCR, 5 µL of the PCR products were taken for agarose gel electrophoresis detection. A 1.5% agarose gel was prepared and were stained in ethidium bromide (EB) for 10 min after electrophoresis for 25 min and photographed in an ultraviolet gel imaging system.

(4) Determination of Results

The materials producing amplification band of 333 bp were transgenic positive plants, and the materials not producing such an amplification band were transgenic negative plants.

The above transgenic positive plants, i.e., T0 generation plants, were transplanted into large flowerpots.

Example 3. Identification of Transgenic Maize Resistance

The T0 generation plants were self-crossed and the resulting seeds were T1 generation seeds. T1 generation seeds were sown in a greenhouse to obtain T1 generation plants. The above procedure was repeated until the T4 generation seeds were obtained.

Transgenic positive detection, herbicide resistance analysis, insect resistance identification, and agronomic trait analysis were performed on the T1 to T3 generation plants. Plants that were transgenic positive, insect-resistant, and herbicide-resistant, and exhibited excellent agronomic traits from each generation were selected for next generation screening.

1. Positive Detection

The detection method and procedure were the same as those described in Example 2.

2. Identification of Herbicide Resistance

The self-crossed seeds from positive plants in step 1 were planted in a greenhouse, and plants at 6-8 leaf stage were subjected to herbicide resistance identification to remove plants that were not resistant to herbicides.

(1) Identification of Glufosinate Resistance

The glufosinate herbicide "Basta" used for spraying was produced by Bayer Crop Science (China) Co., Ltd., with an effective ingredient of 18% glufosinate as a solution. The herbicide was recommended to use in an amount of 200-300 ml/mu, and the herbicide was sprayed in an amount of 250 ml/mu, which was the median of the recommended concentration. Herbicide resistance was observed and recorded after 4-5 days. Maize plants resistant to glufosinate grew normally without any injured symptoms; maize plants sensitive to glufosinate showed significant herbicide damage symptoms, including growth arrest, chlorosis, blotch, malformation, etc., until the whole plants died.

In the $T_1$, $T_2$ and $T_3$ generation plant populations, a Chi-squared test was performed according to the following formula: $\chi^2 = \Sigma[(|o-e|-0.5)^2/e]$, based on the actual separation ratio observed for glufosinate resistance and the expected separation ratio calculated according to Mendelian genetic law (Table 1); where "o" is the observed value of positive or negative plant number, "e" is the expectancy value of positive or negative plant number, and "0.5" is Yates analysis correction factor when degree of freedom is 1.

TABLE 1

Expected Separation Ratios for Various Generations of Transformant ZZM030

| Generation | Expected separation ratio * | Description |
|---|---|---|
| $T_1$ | 3:1 | Positive: Negative (self-crossing separation) |
| $T_2$ | 3:1 | Positive: Negative (self-crossing separation) |
| $T_3$ | 1:0 | Positive: Negative (homozygous plant) |

*: Expected separation ratios were calculated according to Mendelian genetic law in the case of a single copy inserted into a single site.

TABLE 2

Separation Analysis of Various Generations of Transformant ZZM030 -$\chi^2$ Test

| Generation | Total number of plants | Observed value (o) | | Expected value (e) | | $\chi^2$ | $\chi^2_{0.05, 1}$ | Probability (P) |
|---|---|---|---|---|---|---|---|---|
| | | Number of positive plants | Number of negative plants | Number of positive plants | Number of negative plants | | | |
| T1 | 7 | 5 | 2 | 5.25 | 1.75 | 0.0476 | 3.84 | >0.05 |
| T2 | 29 | 24 | 5 | 21.75 | 7.25 | 0.5632 | 3.84 | >0.05 |
| T3 | 76 | 76 | 0 | 76 | 0 | No separation | — | — |

In Table 2, "observed value" is the actual number of positive plants and the number of negative plants observed after spraying with glufosinate; "expected value" is the theoretical number of transgene-positive plants and transgene-negative plants calculated according to Mendelian genetic law according to Table 1; "$\chi^2$" is the Chi square value calculated according to the Chi square test formula; "$\chi^2_{0.05, 1}$" is a value obtained by looking up the $\chi^2$ table with the significance level $\alpha=0.05$ and degree of freedom of 1; "probability" is the result of a comparison between $\chi^2$ and $\chi^2_{0.05,1}$. When $\chi^2 < \chi^2_{0.05,1}$, then P>0.05, indicating that there was no significant difference between the observed value and the expected value. $\chi^2$ test analysis in Table 2 showed that there was no significant difference between the observed separation ratio and the expected separation ratio in the $T_1$-$T_3$ survey generations (P>0.05), indicating that ZZM030 was stably inherited according to Mendelian genetic law between generations and reached homozygosity in the $T_3$ generation.

(2) Identification of Glyphosate Resistance

The glyphosate herbicide "Roundup" used for spraying was produced by Monsanto Corporation with an active ingredient of 41% isopropylamine salt. The herbicide was recommended to be used in maize field in an amount of 150-250 ml/mu, and the herbicide was sprayed in an amount of 200 ml/mu, which was the median of the recommended concentration. Herbicide resistance was observed and recorded after one week. Maize plants resistant to glyphosate grew normally without any injured symptoms; maize plants sensitive to glyphosate showed significant herbicide damage symptoms, including growth arrest, chlorosis, blotch, malformation, etc., until the whole plants died.

3. Identification of Corn Borer Resistance of Transgenic Maize Plant

The corn borer resistance of plants in the field was identified by live worm inoculation method at whorl stage of the maize.

The inoculation was carried out when the maize plants were grown to the middle of the whorl stage (7 leaf stage). The test insects were *Ostrinia furnacalis*, in which approximately 60 black-headed eggs were placed in a centrifuge tube and the tube orifice was occluded with defatted cotton. The centrifuge tube was placed in a 28° C. incubator with a humidity of 80%, or placed in a room temperature condition and covered with a wet towel for moisturization. After hatching the eggs, the defatted cotton was removed and the hatched eggs were placed into the heart leaf cluster. Each plant was inoculated with 40-60 worms. At 2-3 weeks after inoculation, the extent of damage to the heart leaf of the plant was investigated, and the damage grade was classified according to the size and the number of the pest holes on the damaged leaves, and referred to as the leaf-eating grade. The present application employed a 9 grading standard developed by the International Corn borer Collaboration (Table 1). The leaf-eating grades were investigated on a plant-by-plant basis, with the average of each plant as the leaf-eating grade for the identified line, and their resistance to borer was determined according to the evaluation criteria of Table 3.

TABLE 3

Field evaluation criteria for maize bore resistance

| Shape of damaged heart leaf | | Leaf-eating grade | Damage to stems (hole/plant*) | Borer resistance type ** |
|---|---|---|---|---|
| Needle-like or pinhole sized wormhole | Several leaves, rare, dispersed | 1 | 0-2 | HR |
| | Several leaves, medium number | 2 | 0-2 | HR |
| | A few leaves, a large number | 3 | 0-2 | R |
| Mung bean-sized wormhole, some leaves exhibiting short striped-holes | Several leaves, rare, dispersed | 4 | 0-2 | R |
| | Few leaves, medium number | 5 | 3-5 | MR |
| | Some leaves, a large number | 6 | 3-5 | MR |
| Wormhole larger than mung bean, leaves having rows of holes, long-striped-holes, with withered center | Few leaves, rare, dispersed | 7 | 3-5 | S |
| | Some leaves, medium number | 8 | 3-5 | S |
| | Most leaves, a large number | 9 | >6 | HS |

Note:
*1 hole in tunnel 2.5 cm when assessing damage to stems.
** HR: High resistance;
R: Resistance;
MR: Moderate resistance;
S: Sensitivity;
HS: High Sensitivity 4. Maize Transformation Event ZZM030

The maize transformation event ZZM030 was finally screened out.

FIG. 2 is a photograph of plants at 4-5 days after spraying the glufosinate herbicide "Basta" in an amount of 250 ml/mu, in which FIG. 2A is ZZM030 which grew normally without any injured symptoms, and FIG. 2B is a wild-type control, Xiang 249, the leaves of which are dry, chlorotic and stagnant, showing a significant injured symptoms. The results showed that this event showed high resistance to the glufosinate herbicide.

FIG. 3 is a photograph of plants at one week after spraying the glyphosate herbicide "Nongda" in an amount of 200 ml/mu, in which FIG. 3A is ZZM030 which grew normally without any injured symptoms. FIG. 3B shows a wild-type control, Xiang 249, the leaves of which are dry, chlorotic and stagnant, showing a significantly injured symptoms. The results showed that this event showed high resistance to the glyphosate herbicide.

FIG. 4 is a photograph of a field experiment for the identification of corn borer (Asian corn borer) resistance by using a leaf-stage in vivo inoculation method, with white spots as wormholes. FIG. 4A showed the ZZM030 leaf with sparse and dispersed pinhole-sized wormholes. FIG. 4B showed a non-transgenic negative control, Xiang 249 leaf with mung bean-sized wormhole, with some leaves exhibiting short striped-holes. This event was shown to have a high resistance level to Asian corn borer, with an average leaf-eating grade of 1.2-1.5 (see Table 4).

TABLE 4

Results of leaf-eating grade bioassay of different generations of transformants

| Generation | Field number | Average leaf-eating grade | Standard deviation |
|---|---|---|---|
| T1 | TM151X05U1005070 | 1.2* | 0.4 |
| T2 | TM152X05U2007028 | 1.5* | 0.7 |
| T3 | TM153X05U3007014 | 1.2* | 0.5 |
| Negative control | CK-M | 6.1 | 1.1 |

Note:
The number of investigated plants n = 10;
"*"represents a significant difference compared to the negative control.

Example 4. Identification of Armyworm Resistance of Maize Transformation Event ZZM030

1) Armyworm Resistance Ex-Vivo Bioassay I

The commercial transgenic maize variety Bt11 from Syngenta, which contains the Cry1Ab gene and has been reported to be resistant to armyworms, was used as a positive control; The recipient material Xiang 249 used for constructing the transgenic event was used as a negative control; The ex-vivo bioassay was performed on transformation event ZZM030 for its resistance to armyworm; The test armyworm was *Mythimna separate* (Walker).

Specific identification methods were as follows: Fresh maize plants grown to 3-4 and 8-10 leaf stages, respectively, were brought into a room, young heart leaves were taken and placed in a culture dish, and 10 1-day-old insects were inoculated; Each dish was subject to one treatment, and each treatment was repeated three times; The culture dishes were incubated in an artificial climate chamber at 28±1° C. with photoperiod of 14:10h (L:D), and relative humidity of 70-80%. After 3 days, the number of live larvae was counted and the survival rate of the larvae was calculated.

The survival rates of armyworms on different maize varieties were analyzed by multiple comparison with the significant level of 0.05. The survival rate was subjected to a square and inverse sine transformation prior to statistical analysis, and the difference significance between the treatments were compared. According to the difference significance of the survival rate of the larvae fed on the transgenic maize and the control maize, their armyworm resistance was qualitatively determined with reference to Table 5, and the identification results were shown in Table 6.

TABLE 5

Evaluation criteria of *Mythimna Separate Ex-vivo* Bioassay

| Resistance level | Larval survival (Y)% |
|---|---|
| High Resistance | Y ≤ 10 |
| Resistance | 10 < Y ≤ 20 |
| Moderate Resistance | 20 < Y ≤ 45 |

TABLE 5-continued

Evaluation criteria of *Mythimna Separate Ex-vivo* Bioassay

| Resistance level | Larval survival (Y)% |
|---|---|
| Sensitivity | $45 < Y \leq 60$ |
| High Sensitivity | $60 < Y$, close to control or the same |

TABLE 6

Ex-vivo Bioassay Results of Armyworm Resistance of Different Maize Materials

| Material name | Survival (%) | Resistance level |
|---|---|---|
| ZZM030 | 22.55 | Moderate Resistance |
| Bt11 | 2.94 | High Resistance |
| Xiang 249 | 70.00 | High Sensitivity |

2) Armyworm Resistance Ex-Vivo Bioassay II

The commercial transgenic maize variety Bt11 from Syngenta, which contains the Cry1Ab gene and has been reported to be resistant to armyworms, was used as a positive control; The recipient material Xiang 249 used for constructing the transgenic event and the conventional maize, on which various generations of armyworms (studied by Migratory Pest Research Group, Plant Protection Research Institute, Chinese Academy of Agricultural Sciences) fed, were used as a negative control; The ex-vivo bioassay was performed on the transformation event ZZM030 for its resistance to armyworms; The test armyworm was *Mythimna separate* (Walker).

Specific identification methods were as follows: Fresh leaves at the 3-4 and 8-10 leaf stages were selected as food for the test armyworm; All the maize leaves were sterilized by being soaked in 0.1% sodium hypochlorite solution for 3 min and then washed with distilled water and air-dried; The whole maize plant was placed in a canned bottle of 750 ml, and 40 newly hatched larvae were placed therein. Each treatment was repeated three times; The bottles were placed in an artificial climate chamber at a temperature of $(24\pm1°)$ C. with humidity of $(70\pm5)\%$, and photoperiod of 14L:10D; Fresh maize plants which had received corresponding treatments were replaced every 2 days and larvae were examined for death on days 3, 6, and 9 after the start of the test, respectively.

The survival data of larvae receiving different treatments on days 3, 6, and 9 were sorted by Excel, and variance analysis was performed for the survival rates of larvae receiving different treatments by using SPSS software (SPSS 16.0) of SPSS Inc. of the United States of America. If the difference was significant, and then multiple comparisons were made using Tukey's HSD. Survival data were subjected to a square and inverse sine transformation prior to statistical analysis.

Table 7 shows the effect of different materials at 3-4 leaf stage on the survival rate of freshly hatched armyworms. The data in the Table are mean±standard error. The same letter in the same column indicates that there is no significant difference at the $P<0.05$ level by the Tukey's HSD test. The survival rates of the larvae of the armyworms on the conventional maize plantlets were more than 95% after treatment and on days 3, 6 and 9, indicating that the insects used in the experiment were healthy and the experiment was feasible. The survival rates of the newly hatched larvae were significantly affected by the different materials at 3-4 leaf stage. The survival rates of the larvae on each material on the third day were higher, and except that the survival rate of the Bt11 larvae was significantly lower than that of other materials ($P<0.05$), there was no significant difference between other treatments ($P>0.05$). On day 6, the difference in larval survival was even more significant among the treatments, and in particular the Bt11 larval survival decreased significantly, only to 31.7%, the resistance level of which was moderate according to the evaluation criteria of Table 5. On day 9, the difference of larval survival among treatments was further increased.

TABLE 7

Effect of Different Materials at 3-4 Leaf Stage on Survival Rate of Newly hatched Armyworms

| Material name | Day 3 survival | Day 6 survival | Day 9 survival |
|---|---|---|---|
| ZZM030 | (98.33 ± 0.83) a | (75.0 ± 5.00) b | (55.83 ± 3.60) b |
| Bt11 | (82.5 ± 3.81) b | (31.7 ± 1.67) d | (16.17 ± 2.23) c |
| Xiang 249 | (100 ± 0.00) a | (98.3 ± 0.83) a | (90.83 ± 1.72) a |
| Conventional maize | (98.33 ± 1.67) a | (97.5 ± 1.44) a | (95.83 ± 2.22) a |

Table 8 shows the effect of different materials at 8-10 leaf stage on the survival rate of freshly hatched armyworms. The data in the Table are mean±standard error. The same letter in the same column indicates that there is no significant difference at the $P<0.05$ level by the Tukey's HSD test. The survival rate of Bt11 larval was significantly lower than that of Xiang 249 and conventional maize plantlets on 3 day after the test. The difference among larval survival rates at day 6 after treatment was significantly increased: the survival rate of larvae on ZZM030 was lower than 45%, showing a moderate resistance; Xiang 249 and conventional maize plantlets showed high sensitivity. On 9 days after treatment, Xiang 249 and conventional maize plantlets showed high sensitivity in terms of the larval survival rate and were significantly higher than other materials; ZZM030 showed high resistance.

TABLE 8

Effect of Different Materials at 8-10 Leaf Stage on Survival Rate of Newly hatched Armyworms

| Material name | Day 3 survival | Day 6 survival | Day 9 survival |
|---|---|---|---|
| ZZM030 | (70.00 ± 9.46) ab | (21.67 ± 3.63) cd | (8.33 ± 0.83) c |
| Bt11 | (57.50 ± 1.64) b | (20.83 ± 6.51) cd | (6.67 ± 3.63) c |
| Xiang 249 | (99.17 ± 0.83) a | (98.33 ± 1.67) a | (93.33 ± 3.00) a |
| Conventional maize | (99.17 ± 0.83) a | (98.33 ± 0.83) a | (91.67 ± 0.83) a |

3) Identification of Resistance of Armyworms in the Field

Three experimental locations were set up in Gong Zhong ling (Jilin), Yin ma Quan (Jinan) and Jing Hong (Yunnan) to identify the resistance of ZZM030 in the field to armyworms in the form of living insects. Xiang 249 was used as a control and the test armyworms were *Mythimna separate* (Walker).

The inoculation method was: 4-6 leaf stage, 40 plants per location, 40 newly hatched larvae per plant; Inoculation was performed twice with 3 day interval; On day 14 after the last inoculation, leaf-eating grades of plants inoculated by larvae in each location were investigated and the resistance levels of the materials at whorl stage were evaluated according to the criteria. The grading criteria and the resistance level determination criteria were performed in accordance with the provisions of the Ministry of Agriculture Publication No. 953-10.1-2007.

The identification results were shown in Table 9 and FIG. 5. In Table 9, the values are expressed as the mean±standard deviation of 3 replicates, and the lowercase letters in the same column indicate significant differences between different materials at the same location (P<0.01). In FIG. 5, A is the transgenic event ZZM030 and B is the negative control 249. The edge of the leaf and the missing part of the leaf are the wormholes after being eaten by the armyworms. In the test location of Gong Zhong ling, the ZZM030 had an average leaf-eating grade of 1.2 and high resistance, and the negative control recipient maize Xiang 249 had an average leaf-eating grade of 5.8 and moderate resistance; In the test location of Jinan, the ZZM030 had an average leaf-eating grade of 2.7, and resistance, and the negative control recipient maize Xiang 249 had an average leaf-eating grade of 5.4, and moderate resistance. In the test location of Jing Hong, the ZZM030 had an average leaf-eating grade of 1.5 and high resistance, and the negative control recipient maize Xiang 249 had an average leaf-eating grade of 9.0 and high resistance. The resistance of the transformation event ZZM030 to armyworms was significantly different from that of the negative control (the recipient maize Xiang 249) at three test locations, indicating that the transformation event ZZM030 at the 4-6 leaf stage had better resistance to armyworms under field conditions.

TABLE 9

Identification of Resistance of Different Materials in the Field

| Test location | Material name | Average leaf-eating grade | Resistance type |
|---|---|---|---|
| Gong Zhu Ling | ZZM030 | 1.2 ± 0.2 B | High resistance (HR) |
| | Xiang 249 | 5.8 ± 0.4 A | Moderate resistance (MR) |
| Yin ma Quan | ZZM030 | 2.7 ± 0.2 C | Resistance (R) |
| | Xiang 249 | 5.4 ± 0.2 B | Moderate resistance (MR) |
| Jing Hong | ZZM030 | 1.5 ± 0.3 B | High resistance (HR) |
| | Xiang 249 | 9.0 ± 0.0 A | High sensitivity (HS) |

Example 5. Identification of Maize Transformation Event ZZM030 Via Southern Blotting 1. Preparation of Probes
(1) Preparation of cry1Ab/cry1AcZM Probe A probe was prepared using pZHZH35006 plasmid DNA as a template. The probe for detecting cry1Ab/cry1AcZM was synthesized by using the PCR digoxin probe synthesis kit from Roche (Cat. No. 11636090910) with the primers CSP759 (SEQ ID NO 2) and CSP760 (SEQ ID NO 3). The probe size was 333 bp (the probe sequence corresponds to the nucleotide sequence at positions 6084-6416 of SEQ ID NO: 1). The amplification system comprised: DNA template 5 μL (50 μg), primers each 0.5 PCR DIG mixture 5 μL, DNA polymerase 0.75 PCR buffer (10-fold) 5 μL, ddH$_2$O 33.25 μL. The PCR reaction procedure was: pre-denaturation at 94° C. for 5 min; 35 cycles: denaturation at 94° C. for 30 sec, annealing at 55° C. for 30 sec, extension at 72° C. for 45 sec; Finally, extension at 72° C. for 7 min. The amplification effects were detected using 1% agarose gel. The specific amplification product, i.e., the probe for detecting cry 1Ab/cry 1AcZM, were stored at −20° C.

(2) Preparation of Bar Probe

Using the method described in (1), a specific probe for the bar gene was prepared using a primer pair (SEQ ID NO: 4: FW-Csp73, SEQ ID NO: 5: RV Csp74) with a length of 408 bp (the probe sequence corresponds to the nucleotide sequence at positions 1035-1442 of SEQ ID NO: 1).

(3) Preparation of Cp4 epspsZM Probe

Using the method described in (1), a specific probe for the cp4 epspsZM gene was prepared using a primer pair (SEQ ID NO: 6: FW-Csp1337, SEQ ID NO: 7: RV-Csp1338) with a length of 1138 bp (the probe sequence corresponds to the nucleotide sequence at positions 9058-10195 of SEQ ID NO: 1).

2. DNA Extraction

The total genomic DNA of the leaves of the transgenic maize $T_1$, $T_2$, or $T_3$ generation materials was extracted, and the obtained DNA precipitate was dried and dissolved in non-ionic water. The concentration was determined for later use.

3. Enzymatic Digestion, Electrophoresis, Transmembrane, and Development

When the cry1Ab/cry1AcZM probe was used, the maize genomic DNA was single-digested with HindIII or Kprd.

When the bar probe was used, the maize genomic DNA was single-digested with HindIII or EcoRI.

When the cp4 epspsZM probe was used, the maize genomic DNA was single-digested with HindIII or Kprd.

A 200 μL digestion system was used, which contained 20 μg maize genomic DNA, 20 μl restriction enzyme, 20 μL 10-fold buffer and was supplemented with ddH$_2$O to 200 μL. The DNA was digested for 16 h, and then 20 μL was taken for electrophoresis to determine whether the enzyme digestion was complete.

The digested product was supplemented with ddH$_2$O to 400 μL, and 1/10 volume of 3 M sodium acetate solution (pH 5.2) was added, following by adding 4 μL of TaKaRa Dr. GenTLE Precipitation Carrier and 2.5-fold volumes of absolute ethanol. It was mixed well and centrifuged at 12,000 rpm at 4° C. for 15 min. The precipitate was dissolved in 50 ddH$_2$O and 5 μL 6× loading buffer was added.

The DNA was subjected to electrophoresis in a 0.8% gel at 20V for 16 h. Excess lanes and loading wells were cut off and the remaining gels was treated twice with denaturing solution for 15 min each time and shaken gently on a shaker. The gels were treated twice with neutralization buffer for 15 min each time and shaken gently on a shaker. The gels were washed once with ultrapure water. After 20×SSC treatment for 10 min, the DNA was transferred to the membrane for 4 hours or more with the Whatman system.

At the end of the membrane transferring, the membrane was placed on a Whatman 3MM filter paper impregnated with 10×SSC, and allowed to be cross-linked for 3-5 min with an ultraviolet crosslinker. The membrane was simply washed with ddH$_2$O and dried in air. The hybridization and development processes were performed according to the instruction manuals of the digoxin detection kit I from Roche (Cat. No. 11745832910) or the digoxin detection kit II from Roche (Cat. No. 11585614910).

4. Analysis of Results

FIG. 6A shows the results of hybridization of the maize genomic DNA of the transformation event ZZM030 digested respectively by HindIII and KpnI to the cry1Ab/cry1AcZM-specific probe molecule. One positive band was shown under the two digestion conditions. The band obtained by HindIII digestion was 10.9 kb, and the band obtained by KpnI digestion was 10.5 kb, indicating a single-copy insertion of the foreign gene cry1Ab/cry1AcZM. The transformation event was a single-copy transformation event.

FIG. 6B shows the results of hybridization of the maize genomic DNA of the transformation event ZZM030 digested respectively by HindIII and EcoRI to the bar-specific probe molecule. One positive band was shown under the two digestion conditions. As expected, the band obtained by HindIII digestion was 4.2 kb, and the band obtained by EcoRI digestion was 10.0 kb, indicating a single-copy insertion of the foreign gene bar. The transformation event was a single-copy transformation event.

FIG. 6C shows the results of hybridization of the maize genomic DNA of the transformation event ZZM030 digested respectively by HindIII and KpnI to the cp4 epspsZM-specific probe molecule. As expected, the band obtained by HindIII digestion was 10.9 kb, and the band obtained by KpnI digestion was 10.5 kb, indicating a single-copy insertion of the foreign gene cp4 epspsZAM. The transformation event was a single-copy transformation event.

Example 6. Sequence Analysis of Maize Transformation Event ZZM030

In a transgenic process, large amounts of genetic transformation were typically carried out using the same transformation vector, and very few excellent transformation events were screened out from the many transformation events obtained. Therefore, the detection of the vector, the expression element, the foreign gene, and the like in the inserted foreign sequence can only prove that the sample to be detected contains the transgenic component and cannot distinguish different transformation events. Different transformation events were characterized by a combination of the flanking sequences of insertion sites and the inserted exogenous sequence. To this end, the flanking sequences of maize transformation events were isolated and identified in this example.

1. Analysis of Left Flanking Sequence

Total DNA was extracted from the leaves of plants (robust $T_2$ or $T_3$ generation of transgenic plants) to be tested for transformation events, and the flanking sequences of the exogenous gene inserted into the maize genome were amplified, cloned and sequenced by the FPNI-PCR method to obtain sequence results.

(1) The Tail-PCR primer sequences are shown in Table 10.

TABLE 10

| Primer sequence | |
|---|---|
| Name | Sequence |
| FP3: | 5'-GTAATACGACTCACTATAGGGCACGCGTGGT WGTGNAGWANCANAGA-3' (primer length 47 bp); |
| FSP1: | 5'-GTAATACGACTCACTATAGGGC-3' (primer length 22 bp) |
| FSP2: | 5'-ACTATAGGGCACGCGTGGT-3' (primer length 19 bp) |
| Bar-86: | 5'-GGAACTGGCATGACGTGGGTTTCT-3' (primer length 24 bp); |

TABLE 10 -continued

| Primer sequence | |
|---|---|
| Name | Sequence |
| Bar-22: | 5'-CCTGCCCGTCACCGAGATTTGA-3' (primer length 22 bp); |
| 35003Left-254-anti | 5'-ATGTGTGAGTAGTTCCCAGATAAG-3' (primer length 24 bp) |

Wherein W = A/T, N = A/G/C/T.

(2) High-quality of maize genomic DNA was prepared and diluted to 100 ng/μL for later use.

(3) The genomic DNA in step (2) was used as a template for the first round of PCR reaction, and the reaction system was shown in Table 11 below. The reaction procedure was: 95° C., 2.5 min; 2 cycles: 94° C., 10 sec, 62° C., 30 sec, 72° C., 2 min; 94° C., 10 sec; 25° C., 2 min; 72° C. (5.1% ramp), 2 min; 5 cycles: 94° C., 10 sec, 62° C., 30 sec, 72° C., 2 min; 94° C., 10 sec; 62° C., 30 sec; 72° C., 2 min; 94° C., 10 sec; 44° C., 30 sec; 72° C., 2 min; 72° C., 5 min; 20° C., 10 min.

TABLE 11

| First round of PCR reaction system | |
|---|---|
| Component | Volume μL |
| 10 × PCR Buffer | 2 |
| DNTP (10 mmol/L) | 0.5 |
| Bar-86 (10 μM) | 0.5 |
| FP3 (10 μM) | 0.5 |
| RTaq (5 U/μL) | 0.5 |
| Genomic DNA | 1 |
| DdH$_2$O | To final volume 20 μL |

(4) A second round of PCR amplification was performed using the first round of PCR product (mixed mother liquor) as a template, and the reaction system was shown in Table 12 below. The reaction procedure was: 94° C., 1.5 min; (94° C., 10 sec; 62° C., 30 sec; 72° C., 2 min)×30 cycles; 72° C., 7 min; 20° C., 10 min.

TABLE 12

| Second round of PCR reaction system | |
|---|---|
| Component | Volume μL |
| 10 × PCR Buffer | 2 |
| DNTP (10 mmol/L) | 0.5 |
| Bar-22 (10 μM) | 0.5 |
| FSP1 (10 μM) | 0.5 |
| RTaq (5 U/μL) | 0.5 |
| Last round of PCR product (mother liquor) | 1 |
| DdH$_2$O | to final volume 20 μL |

(5) A third round of PCR amplification was performed using a second round of PCR product (50-fold dilution of the mixture) as a template, and the reaction system was shown in Table 13 below. The reaction procedure was: 94° C., 1.5 min; (94° C., 10 sec; 62° C., 30 sec; 72° C., 2 min)×30 cycles; 72° C., 7 min; 20° C., 10 min.

TABLE 13

Third round of PCR reaction system

| Component | Volume μL |
|---|---|
| 10 × PCR Buffer | 2 |
| DNTP (10 mmol/L) | 0.5 |
| 35003Left-254-anti (10 μM) | 0.5 |
| FSP2 (10 μM) | 0.5 |
| RTaq (5 U/μL) | 0.5 |
| Last round of PCR product (mother liquor) | 1 |
| DdH$_2$O | to final volume 20 μL |

(6) The products of the third round of PCR were electrophoresed in a 1% (w/v) 1×TAE agarose gel and the DNA fragments between 300 bp-2 kb were recovered.

(7) The recovered fragments were ligated to T-vector overnight at 16° C.

(8) The ligation products of step (7) were transformed.

(9) The transformed products in step (8) were amplified with primers M13F: 5'-TGTAAAACGACGGCCAGT-3' and M13R: 5'-CAGGAAACAGCTATGACC-3'. The positive clones were picked and cultured in a shaker. The plasmid DNA was extracted with TIANprep Rapid Mini Plasmid Kit (centrifugal column type).

(10) The plasmid DNA in step (9) was sequenced with sequencing primers, and the sequencing PCR of the plasmid DNA was performed with BigDye® Terminator v3.1 Cycle Sequencing Kit. Sequencing primers were M13F and M13R primers: M13-F: 5'-TGTAAAACGACGGCCAGT-3', M13-R: 5'-CAGGAAACAGCTATGACC-3'.

(11) PCR products in step (10) were purified with NaAc and absolute ethanol, and denaturated in formamide.

(12) The purified and denatured PCR products in step (11) were sequenced using a ABI DNA sequencer 3730 and the sequencing results were read out.

(13) The sequencing results were searched for the homology with the maize genome sequence in the PlantGDB database using the BLASTN tool, with the best matching result being represented by the chromosome number and base pair position number of the insertion site. The sequence identity was generally 90-100%.

(14) The left flanking sequence 680 bp of the inserted T-DNA was detected by this experiment, as shown in nucleotide positions 1-680 of SEQ ID NO: 1. With the whole genome sequence of maize B73 as a reference (http://www.plantgdb.org/ZmGDB/cgi-bin/blastGDB.pl), analysis and comparison confirmed that the left insertion point of the transformation event of the present application was located on chromosome 4 40636901 bp.

2. Analysis of Right Flanking Sequence

Total DNA was extracted from the leaves of plants (robust T$_2$ or T$_3$ generation of transgenic plants) to be tested for transformation events, and the flanking sequences of the exogenous gene inserted into the maize genome were amplified, cloned and sequenced by the linker PCR method to obtain sequence results.

(1) Primers required for linker PCR were artificially synthesized, and diluted for later use; Primer sequences are shown in Table 14.

TABLE 14

Primer sequence

| Name | Sequence |
|---|---|
| AD-L | 5'-CTAATACGAGTCACTATAGCGCTCGAGCGGC CGCCGGGGAGGT-3' |
| AD-S | 5'-Pi-ACCTCCCC-NH2-3' |
| SP1 | 5'-GGATCCTAATACGAGTCACTATAGCGC-3' (primer length 27 bp); |
| SP2 | 5'-CTATAGCGCTCGAGCGGC-3' (primer length 18 bp); |
| Csp3518 | 5'-CATGGGCCTCGTTTCGGAGA-3' (primer length 20 bp); |
| Csp3519 | 5'-ATGCCACCATGATTGCGACG-3' (primer length 20 bp); |

(2) High-quality of maize genomic DNA was prepared and diluted for later use;

(3) The linker primers AD-L and AD-S were diluted to 100 μmol/L with ddH$_2$O, and mixed in equal volumes, denatured with in water bath at 94° C. for 4 min, and naturally cooled to the room temperature to obtain 50 μmol/L of the linkers.

(4) The maize genomic DNA was digested with the following enzyme system:

| | |
|---|---|
| Genomic DNA | 200 ng |
| *StuI* | 0.5 μL |
| Cutsmart | 1 μL |
| Sterilized ddH$_2$O | to final volume 10 μL |
| Digested at 37° C. for 3 h. | |

(5) The linkers were ligated with the ligating system as follows:

| | |
|---|---|
| Digested genomic DNA | 10 μL |
| Linker 50 μM | 0.2 μL |
| T4 ligase (400 U/μL) | 0.5 μL |
| 10 × buffer | 1.5 μL |
| Sterilized ddH$_2$O | to final volume 15 μL |
| Ligated at 16° C. overnight. | |

(6) The linker ligation products of the genomic DNA in step (5) was used as a template for the first round of PCR reaction, and the reaction system was shown in Table 10 below. The reaction procedure was: 94° C., 5 min; 7 cycles: 94° C., 30 sec, 72° C., 3 min; 32 cycles: 94° C. 30 sec; 67° C., 3 min; 67° C., 7 min; 25° C., 10 min.

TABLE 15

First round of PCR reaction system

| Component | Volume μL |
|---|---|
| 10 × PCR Buffer | 2 |
| DNTP (10 mmol/L) | 0.4 |
| Csp3518 (10 μM) | 0.5 |

TABLE 15-continued

First round of PCR reaction system

| Component | Volume μL |
|---|---|
| SP1 (10 μM) | 0.5 |
| RTaq (5 U/μL) | 0.3 |
| Genomic DNA | 2 |
| DdH$_2$O | To final volume 20 μL |

(7) A second round of PCR amplification was performed using the first round of PCR products (40-fold dilution of the mixture) as a template, and the reaction system was shown in Table 16 below. The reaction procedure was: 94° C., 5 min; 5 cycles: 94° C., 30 sec, 72° C., 3 min; 20 cycles: 94° C., 30 sec, 67° C., 3 min; 67° C., 7 min; 25° C., 10 min.

TABLE 16

Second round of PCR reaction system

| Component | Volume μL |
|---|---|
| 10 × PCR Buffer | 2 |
| DNTP (10 mmol/L) | 0.4 |
| Csp3519 (10 μM) | 0.5 |
| SP2 (10 μM) | 0.5 |
| RTaq (5 U/μL) | 0.3 |
| Last round of PCR product (40-fold dilution) | 2 |
| DdH$_2$O | To final volume 20 μL |

(8) A second round of PCR products were electrophoresed in a 1% (w/v) 1×TAE agarose gel and DNA fragments between 300 bp-2 kb were recovered.

(9) The recovered fragments were ligated to T-vector overnight at 16° C.

(10) The ligation products of step (9) were transformed.

(11) The transformed products in step (10) were amplified with primers M13F and M13R. The positive clones were picked and cultured in a shaker. The plasmid DNA was extracted with TIANprep Rapid Mini Plasmid Kit (centrifugal column type).

(12) The plasmid DNA in step (11) was sequenced with sequencing primers, and the sequencing PCR of the plasmid DNA was performed with BigDye® Terminator v3.1 Cycle Sequencing Kit. Sequencing primers were M13F and M13R primers: M13-F: 5'-TGTAAAACGACGGCCAGT-3', M13-R: 5'-CAGGAAACAGCTATGACC-3'.

(13) PCR products in step (12) were purified with NaAc and absolute ethanol, and denaturated in formamide.

(14) The purified and denatured PCR products in step (13) were sequenced using a ABI DNA sequencer 3730 and the sequencing results were read out.

(15) The sequencing results were searched for the homology with the maize genome sequence in the PlantGDB database using the BLASTN tool, with the best matching result being represented by the chromosome number and base pair position number of the insertion site. The sequence identity was generally 90-100%.

(16) The right flanking sequence 460 bp of the inserted T-DNA was detected by this experiment, as shown in nucleotide positions 10915-11374 of SEQ ID NO: 1. With the whole genome sequence of maize B73 as a reference (http://www.plantgdb.org/ZmGDB/cgi-bin/blastGDB.pl), analysis and comparison confirmed that the right insertion point of the transformation event of the present application was located on chromosome 4 40636883 bp. 3. Size of inserted sequence and its effect on endogenous genome of maize The vector size of the single-copy insertion sequence of the foreign gene of the present application including the left and right border sequences was 10282 bp.

The actual size of the transformation event insertion sequence was determined to be 10235 bp (681-10915 of SEQ ID NO: 1) by sequencing segmented PCR amplification of foreign DNA, and the T-DNA insert was 7 bp deleted with respect to the left end of the expression vector and 40 bp deleted with respect to the right end of the expression vector.

The amplification system comprised: DNA template 2 μL (200 ng), primers each 0.5 μL, DNA polymerase 0.5 PCR buffer (10-fold) 2 μL, ddH$_2$O 14.5 ρL. The PCR reaction procedure was: pre-denaturation at 94° C. for 5 min; 35 cycles: denaturation at 94° C. for 30 sec, annealing at 55° C. for 30 sec, extension at 72° C. for 3 min; Finally, extension at 72° C. for 7 min. The amplification effects were detected using 1% agarose gel. Specifically amplified products, i.e., fragments of interest, were recovered.

The 47 bp nucleotides were located at the boundary sequence of the non-coding region. The deletion did not affect the integrity of the insect-resistant gene cry1Ab/cry1AcZM and the screening markers bar and cp4 epspsZm genes. Alignment analysis of DNA sequences showed that the actually inserted nucleotide sequence of the transformation event was completely identical to the vector sequence without any base mutations.

In addition, the maize genome at the insertion site was a repeating sequence, and the deletion of the 47 bp nucleotides did not destroy any known endogenous functional gene of maize.

Example 7. Detection Method of Maize Transformation Event ZZM030

1. Detection of Left Flanking DNA Sequence:

A pair of primers (SEQ ID NO: 8: FW-csp3758 and SEQ ID NO: 9: RV-csp2344) was designed using left flanking genomic sequence of the maize transformation event and 35S PolyA terminator in the exogenous fragment. A qualitative PCR identification method for the transformation event product was established.

Primers designed according to the left boundary (LB) T-DNA 5' end of the integration site of the exogenous DNA fragment of the maize transformation event ZZM030 were:

(FW-csp3758):
SEQ ID NO: 8
5'-TGATGGTTAATGAGGCAAGA-3'

(RV-csp2344):
SEQ ID NO: 9
5'-TATAGGGTTTCGCTCATGTG-3' (35S PolyA region).

The optimal annealing temperature was determined by temperature gradient PCR for amplification of DNA fragments with the specific primers described above at 50-60° C. The results confirmed that 58° C. was the optimal amplification temperature; The PCR reaction procedure was 95° C., 5 min, 35 cycles (95° C., 30s, 50-60° C., 30s, 72° C., 1 min), 72° C., 7 min. To test the specific amplification of the transformation event with the primers (FW-csp3758; RV-csp2344), different sources of maize DNA were used for PCR amplification.

The PCR reaction condition and procedure were 95° C., 5 min, 35 cycles: 95° C., 30 s, 58° C., 30 s, 72° C., 1 min; 72° C. 7 min. The results showed that only the DNA of this transformation event had a positive result, and other transformation events or negative control maize varieties had negative results, see FIG. 7A. Lanes 1 to 4 were respectively sterile water, Xiang 249 DNA, ZZM030 DNA, and other transformation event DNA with the same vector; Only the band in lane 3 of ZZM030 genomic DNA were clearly visible, and the DNA fragment size 898 bp was consistent with that as expected, and the sequencing results of the DNA fragment were also consistent with those as expected.

2. Detection of Right Flanking DNA Sequence:

A pair of primers (SEQ ID NO: 10: FW-csp3879 and SEQ ID NO: 11: RV-csp3889) was designed using 3cp4 epspsZM in the exogenous fragment and right flanking genomic sequence of the maize transformation event. A qualitative PCR identification method for the transformation event product was established.

Primers designed according to the right boundary (RB) T-DNA 5' end of the integration site of the exogenous DNA fragment of the maize transformation event ZZM030 were:

(FW-csp3879):
SEQ ID NO: 10
5'-AAGATTGAGCTGTCGGATAC-3' (cp4 epspsZM region), (RV-csp3889):
SEQ ID NO: 11
5'-TTTGATCATGTGAGGAACGT-3' (maize genome region).

The optimal annealing temperature was determined by temperature gradient PCR for amplification of DNA fragments with the specific primers described above at 46-61° C. The results confirmed that 58° C. was the optimal amplification temperature; The PCR reaction procedure was 95° C. 5 min; 35 cycles: 95° C., 30 s, 46-61° C., 30 s, 72° C. 1 min; 72° C., 7 min. To test the specific amplification of the transformation event with the primers (FW-csp3879; RV-csp3889), different sources of maize DNA were used for PCR amplification.

PCR reaction condition and procedure were 95° C., 5 min; 35 cycles: 95° C., 30 s, 58° C., 30 s, 72° C., 1 min; 72° C. 7 min. The results showed that only the DNA of this transformation event had a positive result, and other transformation events or negative control maize varieties had negative results, see FIG. 7B. Lanes 1 to 4 were respectively sterile water, Xiang 249 DNA, ZZM030 DNA, and other transformation event DNA with the same vector; Only the band in lane 3 of ZZM030 genomic DNA were clearly visible, and the DNA fragment size 769 bp was consistent with that as expected, and the sequencing results of the DNA fragment were also consistent with those as expected.

The foregoing descriptions are merely preferred embodiments of the present invention. It should be noted that those of ordinary skill in the art may make several modifications and variations without departing from the technical principles of the present invention, which are also considered falling into the scope of the present invention.

What is claimed is:

1. A nucleic acid molecule, which is a sequence comprising the nucleotide positions 381-780, 6239-6338 and 10815-11214 of SEQ ID NO: 1, or a complement thereof.

2. The nucleic acid molecule of claim 1, comprising the following expression cassettes:
   a first expression cassette expressing a glufosinate-resistant gene, the sequence of which is set forth in nucleotide positions 748-2288 of SEQ ID NO: 1;
   a second expression cassette expressing an insect-resistant gene, the sequence of which is set forth in nucleotide positions 2620-6959 of SEQ ID NO: 1; and
   a third expression cassette expressing a glyphosate-resistant gene, the sequence of which is set forth in nucleotide positions 6968-10892 of SEQ ID NO: 1.

3. The nucleic acid molecule of claim 1, which is obtainable by introducing the following expression cassettes into the genome of maize:
   a first expression cassette expressing a glufosinate-resistant gene, the sequence of which is set forth in nucleotide positions 748-2288 of SEQ ID NO: 1;
   a second expression cassette expressing an insect-resistant gene, the sequence of which is set forth in nucleotide positions 2620-6959 of SEQ ID NO: 1; and
   a third expression cassette expressing a glyphosate-resistant gene, the sequence of which is set forth in nucleotide positions 6968-10892 of SEQ ID NO: 1;
   optionally, the nucleic acid molecule is present in maize plants, seeds, plant cells, progeny plants or plant parts.

4. A probe for detecting a maize transformation event comprising the nucleic acid molecule of claim 1.

5. A primer pair for detecting a maize transformation event that is capable of specifically amplifying the nucleic acid molecule of claim 1;
   optionally, the primer pair is:
   i) a primer pair that specifically recognizes a sequence comprising nucleotide positions 381-780 of SEQ ID NO: 1;
   ii) a primer pair that specifically recognizes a sequence comprising nucleotide positions 10815-11214 of SEQ ID NO: 1;
   iii) a forward primer that specifically recognizes a sequence comprising nucleotide positions 381-780 of SEQ ID NO: 1, and a reverse primer that specifically recognizes a sequence comprising nucleotide positions 681-10915 of SEQ ID NO: 1; or
   iv) a forward primer that specifically recognizes a sequence comprising nucleotide positions 681-10915 of SEQ ID NO: 1, and a reverse primer that specifically recognizes a sequence comprising nucleotide positions 10815-11214 of SEQ ID NO: 1;
   optionally, the primer pair is the nucleotide sequence as set forth in SEQ ID NO:8 and SEQ ID NO: 9 or a complement thereof; or the nucleotide sequence as set forth in SEQ ID NO:10 and SEQ ID NO:11 or a complement thereof.

6. A kit or microarray for detecting a maize transformation event comprising the probe of claim 4.

7. A method of detecting a maize transformation event comprising detecting the presence or absence of the transformation event in a sample to be detected using the probe of claim 4.

8. A kit or microarray for detecting a maize transformation event comprising the primer pair of claim 5.

9. A method of detecting a maize transformation event comprising detecting the presence or absence of the transformation event in a sample to be detected using the primer pair of claim 5.

10. A method of detecting a maize transformation event comprising detecting the presence or absence of the transformation event in a sample to be detected using the kit or microarray of claim 6.

11. A method of detecting a maize transformation event comprising detecting the presence or absence of the transformation event in a sample to be detected using the kit or microarray of claim 8.

12. The nucleic acid molecule of claim 1, which is a sequence comprising SEQ ID NO: 1, or a complement thereof.

* * * * *